United States Patent
Lammert et al.

(10) Patent No.: US 10,464,904 B2
(45) Date of Patent: Nov. 5, 2019

(54) DEXTRORPHAN-DERIVATIVES WITH SUPPRESSED CENTRAL NERVOUS ACTIVITY

(71) Applicant: Heinrich-Heine-Universität Düsseldorf, Düsseldorf (DE)

(72) Inventors: Eckhard Lammert, Dusseldorf (DE); Alena Welters, Köln (DE); Silke Otter, Duisburg (DE); Jan Marquard, Mainz (DE); Thomas Meissner, Mettmann (DE); Diran Herebian, Düsseldorf (DE); Ertan Mayatepek, Düsseldorf (DE)

(73) Assignee: Heinrich-Heine-Universitat Dusseldorf, Dusseldorf (DE)

( * ) Notice: Subject to any disclaimer, the term of this patent is extended or adjusted under 35 U.S.C. 154(b) by 0 days.

(21) Appl. No.: 15/780,850

(22) PCT Filed: Dec. 2, 2016

(86) PCT No.: PCT/EP2016/079645
§ 371 (c)(1),
(2) Date: Jun. 1, 2018

(87) PCT Pub. No.: WO2017/093519
PCT Pub. Date: Jun. 8, 2017

(65) Prior Publication Data
US 2018/0362469 A1 Dec. 20, 2018

(30) Foreign Application Priority Data
Dec. 3, 2015 (EP) ...................................... 15197832

(51) Int. Cl.
| C07D 221/18 | (2006.01) |
| A61K 31/439 | (2006.01) |
| C07D 221/28 | (2006.01) |
| C07D 401/04 | (2006.01) |
| A61P 3/10 | (2006.01) |

(52) U.S. Cl.
CPC .............. *C07D 221/28* (2013.01); *A61P 3/10* (2018.01); *C07D 401/04* (2013.01)

(58) Field of Classification Search
CPC .............................. C07D 221/28; A61K 31/439

USPC ............................................ 546/74; 514/289
See application file for complete search history.

(56) References Cited

U.S. PATENT DOCUMENTS

2012/0122848 A1 * 5/2012 Lee et al. ............. C07D 221/28
546/74

FOREIGN PATENT DOCUMENTS

| JP | 60089474 A | * 10/1983 | ........... C07D 221/28 |
| JP | 6089474 A | 5/1985 | |
| WO | 2008097924 A2 | 8/2008 | |
| WO | 2011014003 A2 | 2/2011 | |
| WO | 2011142620 A2 | 11/2011 | |
| WO | 2013029762 A1 | 3/2013 | |
| WO | 2016182840 A1 | 11/2016 | |

OTHER PUBLICATIONS

Boccardi G et al: "Photochemical Iron(III)-Mediated Autoxidation of Dextromethorphan", Chemical and Pharmaceutical Bulletin, Pharmaceutical Society of Japan, JP, vol. 37, No. 2, Jan. 1, 1989 (Jan. 1, 1989), pp. 308-310, XP001246659, ISSN: 0009-2363.
Dixon, Ross et al: "Dextromethorphan: radioimmunoassay and pharmacokinetics in the dog", Research Communications in Chemical Pathology and Pharmacology, 22(2), 243-55 CODEN: RCOCB8; ISSN: 0034-5164, 1978, XP009188418.
Grewe, Rudolf et al: "Total synthesis of tetrahydrodesoxycodeine", Annalen Der Chemie, Justus Liebigs , 564, 161-98 CODEN: 9X224Y, 1949, XP009188412.
Peng et al: "In-vitro investigation of oxazol and urea analogues of morphinan at opioid receptors", Bioorganic & Medicinal Chemistry, Pergamon, GB, vol. 15, No. 12, May 5, 2007 (May 5, 2007), pp. 4106-4112, XP022062544, ISSN: 0968-0896, Doi: 10.1016/J.BMC. 2007.03.076.
European Search Report dated Feb. 16, 2017, Application No. EP15197832.7.

* cited by examiner

*Primary Examiner* — Charanjit Aulakh
(74) *Attorney, Agent, or Firm* — The Dobrusin Law Firm, PC

(57) ABSTRACT

The invention relates to dextrorphan-derivatives, pharmaceutical compositions and pharmaceutical dosage forms containing such dextrorphan-derivatives as well as the use of those dextrorphan-derivatives and/or compositions for treating and preventing diseases and conditions in man and mammals.

12 Claims, 11 Drawing Sheets

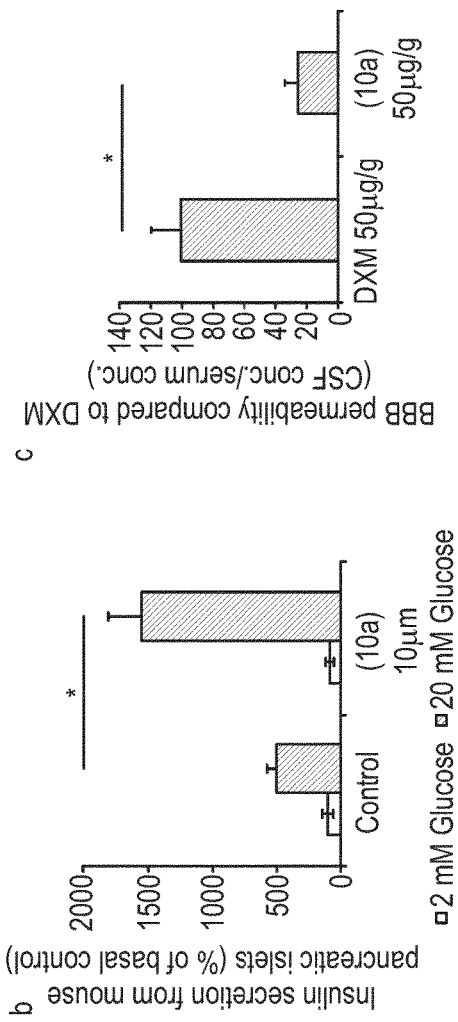
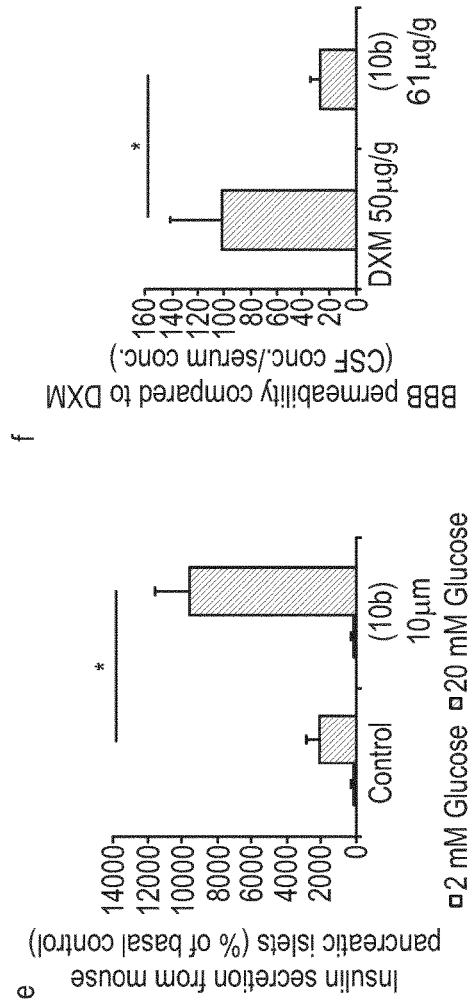
Fig. 8a-c
Fig. 8d-f

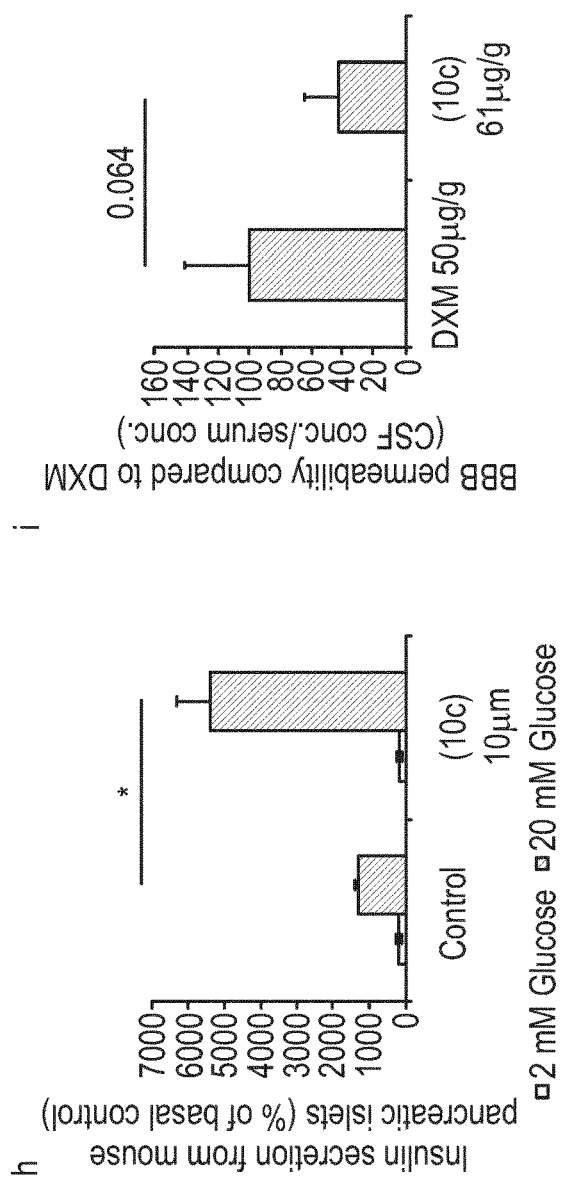
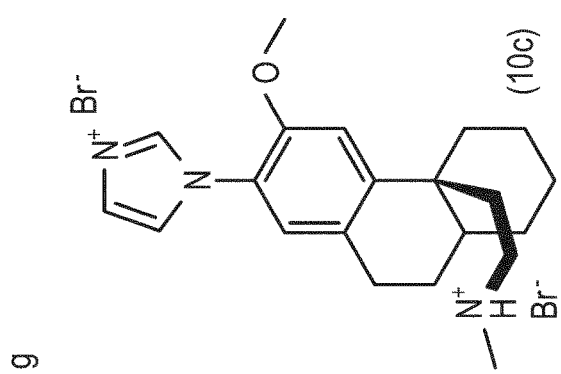
Fig. 8g-i

DEXTRORPHAN-DERIVATIVES WITH SUPPRESSED CENTRAL NERVOUS ACTIVITY

FIELD OF INVENTION

The invention relates to dextrorphan-derivatives, pharmaceutical compositions and pharmaceutical dosage forms containing such dextrorphan-derivatives as well as the use of those dextrorphan-derivatives and/or compositions for treating diseases and conditions in man and other mammals.

BACKGROUND OF THE INVENTION

N-methyl-D-aspartate (NMDA) receptor antagonists such as dextromethorphan are particularly useful for blocking NMDA receptors in the central nervous system (CNS), e.g. to suppress coughing. Besides central nervous activity of NMDA receptor antagonists, their activity in peripheral tissue has attracted attention in clinical research over the last years.
WO 2013/029762 discloses that dextromethorphan and other morphinan-derivatives target NMDA receptors on pancreatic islets for use in the treatment of insulin-dependent diabetes mellitus, non-insulin-dependent diabetes mellitus, obesity, and/or diabetic nephropathy (see Marquard et al., Nat. Med. 2015; 21:363-372; see also Ashcroft et al., Cell 2012; 148: 1160-1171). Dextromethorphan has also been successfully used in the treatment of neuropathic pain, such a diabetic neuropathy (see Zhou et al., Expert Rev Clin Pharmacol 2011; 4: 379-388; Shaibani et al., Pain Med 2012; 13: 243-254). Further, recent preclinical studies revealed that NMDA receptor antagonists may inhibit metastasis and tumor growth and an elevated coexpression of NMDA receptors and glutamate exporters in cancer cells correlates with a poor prognosis for cancer patients (see Li et al., Cell 2013; 153: 86-100).
For inhibiting NMDA receptors in peripheral tissues, such as pancreatic islets or cancer cells, it would be desirable to suppress the central activity of NMDA receptor antagonists in order to reduce the frequency and intensity of central nervous adverse effects as observed upon administration of elevated doses of NMDA receptor antagonists, such as dextromethorphan (Marquard et al., Nat. Med. 2015; 21:363-372). The occurrence of central nervous adverse effects, the risk of a so far incalculable long-term neurotoxicity, as well as a potential development of dependency, which may occur in treatment with conventional NMDA receptor antagonists, make it problematic to use NMDA receptor antagonists at higher concentrations over an extended treatment period (see Logan et al., J Anal Toxicol 2009; 33: 99-103; Olney et al., Science 1989; 244: 1360-2; Zhou et al., Expert Rev Clin Pharmacol 2011; 4: 379-388).
WO 2011/014003 discloses a (+)-3-hydroxymorphinan derivative and a pharmaceutical composition comprising the same as an active ingredient, which are useful for preventing or treating a neurodegenerative disease, are provided.
WO 2011/142620 discloses a (+)-3-hydroxymorphinan-based polycycle derivative as a neuroprotective agent for neurodegenerative diseases including Alzheimers's disease, Parkinson's disease, Huntington's disease, amyotrophic lateral sclerosis and ischemic stroke.
WO 2013/029762 relates to a morphinan-derivative that targets NMDA receptors on pancreatic islets. For use in the treatment of a disease or condition, where the disease or condition is insulin-dependent diabetes mellitus, non-insulin-dependent diabetes mellitus, obesity, and/or diabetic nephropathy.
JP S60 89474 discloses a morphinan-derivative for use as an antitumor agent.
R. Grewe et al., "Die Totalsynthese des Tetrahydrodesoxycodeins", Annalen der Chemie, vol. 564, p. 161-198; relates to the synthesis of tetrahydrodesoxycodein.
G. Boccardi et al., "Photochemical Iron(III)-Mediated Autoxidation of Dextromethorphan", Chem. Pharm. Bull., Pharm. Soc. Japan, vo. 37, no. 2, 1. January 1989, p. 308-310; discloses that the photochemical reaction of dextromethorphan 1 in hydrochloric acid and in the presence of iron(III) salts leads to the 10β-hydroxyderivatives as a major product in addition to the 10-ketoderivative.
Peng et al., "In-vitro investigation of oxazol and urea analogues of morphinan and opioid receptors", Bioorganic and Medicinal Chem., Pergamon, GB, vol. 15, no. 12, 5 May 2007, p. 4106-4112; discloses a series of 2-amino-oxazole analogs and 2-one-oxazole analogs and their evaluation in-vitro by their binding affinity and μ, δ, and κ opioid receptors.
R. Dixon et al., "Dextromorphan: radioimmunoassay and pharmacokinetics in the dog", Research Communications in Chem. Pathology and Pharmacology, vol. 22, no. 2, p. 243-255, relates to the development of a specific radioimmunoassay for the determination of the widely used non-narcotic antitussive agent, dextromethorphan in plasma and urine using an antiserum to dextromethorphan which was obtained from rabbits following immunization with an albumin conjugate of (+)-3-methoxymorphinan-17-succinyloxyethyl.
There is a demand for NMDA receptor antagonists that overcome the drawbacks of the prior art. It is therefore an object of the invention to provide NMDA receptor antagonists that have advantages compared to the prior art.
This object has been achieved by the subject-matter of the patent claims.

SUMMARY OF THE INVENTION

The invention relates to a dextrorphan-derivative according to general formula (I)

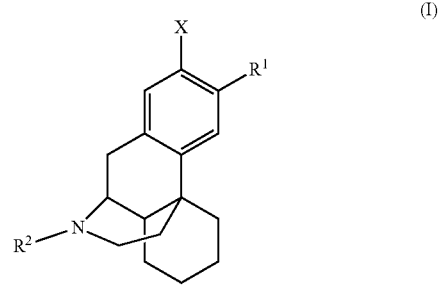

wherein
$R^1$ is selected from —OH, —$CO_2H$, —$R^o$, —$OR^o$, —OC(=O)$R^o$, —OC(=O)$OR^o$ or —OC(=O)$NHR^o$; preferably —OH or —$OC_1$-$C_6$-alkyl;
$R^2$ is selected from —H, —$R^o$, —C(=O)$R^o$, —C(=O)$OR^o$, —C(=O)$NHR^o$, or —C(=NH)—NH—C(=NH)—$NH_2$; preferably —$C_1$-$C_6$-alkyl;
X is selected from —F, —Cl, —Br, —I, or —$NR^3R^4$, wherein $R^3$ and $R^4$ are independently of one another selected from —H or —$R^0$; preferably —I or —$NR^3R^4$, wherein $R^3$ and $R^4$ are independently of one another selected from —H or —$C_1$-$C_6$-alkyl or —$C_1$-$C_6$-fluoroalkyl; or wherein $R^3$ and $R^4$ together with the nitrogen atom to which they are attached form a three, four, five, six, or seven membered heterocycloalkyl- or heteroaryl-ring, in each case independently unsubstituted or substituted; preferably $R^3$ and $R^4$ together with the nitrogen atom to which they are attached form a five membered heterocycloalkyl- or heteroaryl-ring, in each case independently unsubstituted or substituted; more preferably $R^3$ and $R^4$ together with the nitrogen atom to which they are attached form a pyrrolidine ring or imidazole ring, in each case independently unsubstituted or substituted;

wherein $R^0$ is in each case independently selected from —$C_1$-$C_6$-alkyl, —$C_1$-$C_6$-fluoroalkyl, -aryl, -heteroaryl, —$C_1$-$C_6$-alkyl-aryl or —$C_1$-$C_6$-alkyl-heteroaryl, in each case independently unsubstituted or substituted; and or its physiologically acceptable salt and/or stereoisomer, including mixtures thereof in all ratios.

In a preferred embodiment, $R^1$ is —OH, —$OCH_3$, substituted or unsubstituted, or —$CH_3$, substituted or unsubstituted; and $R^2$ is —$CH_3$, substituted or unsubstituted; and/or X is selected from the group consisting of —$NH_2$, —$NHCH_3$, —$NHCH_2CH_3$, —$N(CH_3)_2$, —NH—$CH_2$—$CH_2F$, or —NH—$CH_2$—$CHF_2$ Several morphinan-derivatives are known as pharmacologically active substances (cf. B. Y. Wong et al., Neuroscience Letters 1988, 85 (2): 261-6; J. Church et al., Canadian Journal of Physiology and Pharmacology, 1989, 67 (6): 561-7; I. R. Kamel et al., Journal of Neurosurgical Anesthesiology, 2008, 20 (4): 241-8).

It has now been found that in comparison to dextrorphan, the dextrorphan-derivatives according to the invention enrich in the liquor of the CNS to a significantly lower extent. In addition, the neurological test Rotarod, assessing motor coordination, balance and endurance showed that in stark contrast to dextrorphan, some of these dextrorphan-derivatives do not result in any coordination deficits. In spite of their reduced capability of passaging the blood-brain-barrier and introducing neurological adverse events, dextrorphan-derivatives according to the invention are capable of increasing the glucose-stimulated secretion of insulin from pancreatic islets in vitro as well as improving the glucose tolerance of mice in vivo. Furthermore, application of dextrorphan-derivatives according to the invention do not result in obvious behavioral changes in these mice. The dextrorphan-derivatives according to the invention exhibit apparent toxicity neither in vitro nor in vivo, and it is possible to chemically synthesize and purify them. In addition, all these derivatives (most of them bromide salts) can be synthesized from dextromethorphan or dextrorphan as substrates, which are available at high amounts.

BRIEF DESCRIPTION OF THE DRAWINGS

FIG. 8a-c shows the chemical structure and graphical representations of insulin secretion from mouse pancreatic islets and BBB (blood brain barrier) permeability compared to DXM for exemplary compound (10a).

FIG. 8d-f shows the chemical structure and graphical representations of insulin secretion from mouse pancreatic islets and BBB (blood brain barrier) permeability compared to DXM for exemplary compound (10b).

FIG. 8g-i shows the chemical structure and graphical representations of insulin secretion from mouse pancreatic islets and BBB (blood brain barrier) permeability compared to DXM for exemplary compound (10c).

DETAILED DESCRIPTION OF THE INVENTION

Figure 1:
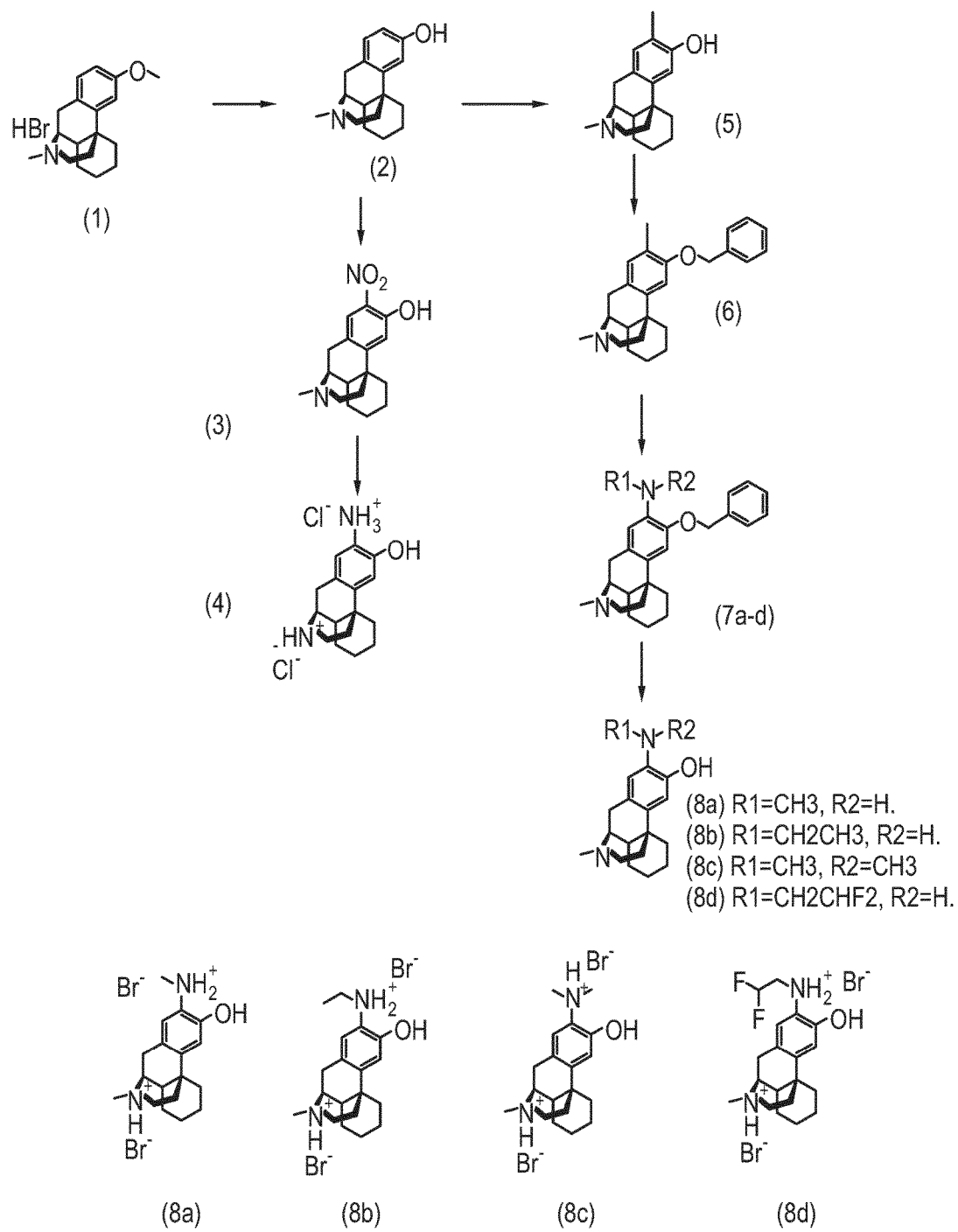
FIG. 1 is a general overview of the route for synthesizing exemplified dextrorphan-derivatives of the present invention.

The invention relates to a dextrorphan-derivative according to general formula (I)

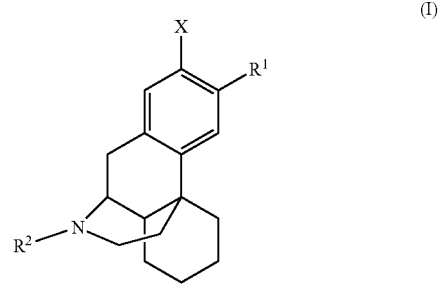

wherein
$R^1$ is selected from —OH, —$CO_2H$, —$R^0$, —$OR^0$, —OC(=O)$R^0$, —OC(=O)$OR^0$ or —OC(=O)$NHR^0$; preferably —OH, —$OC_1$-$C_6$-alkyl, substituted or unsubstituted, or —$C_1$-$C_6$-alkyl, substituted or unsubstituted; preferably —OH, —$OCH_3$, —$OCH_2F$, —$OCHF_2$, —$OCF_3$, —$CH_3$, —$CH_2F$, —$CHF_2$ or —$CF_3$;
$R^2$ is selected from —H, —$R^0$, —C(=O)$R^0$, —C(=O)$OR^0$, —C(=O)$NHR^0$, or —C(=NH)—NH—C(=NH)—$NH_2$;

preferably —C₁-C₆-alkyl, substituted or unsubstituted; preferably —CH₃, —CH₂F, —CHF₂ or —CF₃;

X is selected from —F, —Cl, —Br, —I or —NR³R⁴, wherein R³ and R⁴ are independently of one another selected from —H or —R⁰; preferably —I or —NR³R⁴, wherein R³ and R⁴ are independently of one another selected from —H or —C₁-C₆-alkyl, substituted or unsubstituted; or wherein R³ and R⁴ together with the nitrogen atom to which they are attached form a three, four, five, six, or seven membered heterocycloalkyl- or heteroaryl-ring, in each case independently unsubstituted or substituted; preferably R³ and R⁴ together with the nitrogen atom to which they are attached form a five membered heterocycloalkyl- or heteroaryl-ring, in each case independently unsubstituted or substituted; more preferably R³ and R⁴ together with the nitrogen atom to which they are attached form a pyrrolidine ring or imidazole ring, in each case independently unsubstituted or substituted;

wherein R⁰ is in each case independently selected from —C₁-C₆-alkyl, -aryl, -heteroaryl, —C₁-C₆-alkyl-aryl or —C₁-C₆-alkyl-heteroaryl, in each case independently unsubstituted or substituted; and or its physiologically acceptable salt and/or stereoisomer, including mixtures thereof in all ratios.

In a preferred embodiment, R¹ is —OH, —OCH₃, —OCH₂F, —OCHF₂, —OCF₃, —CH₃, —CH₂F, —CHF₂ or —CF₃; and/or R² is —H, —CH₃, —CH₂F, —CHF₂ or —CF₃.

Preferably, X is —I or —NR³R⁴, wherein R³ and R⁴ are independently of one another selected from —H or —C₁-C₆-alkyl, wherein —C₁-C₆-alkyl is optionally substituted with one or more —F (═—C₁-C₆-fluoroalkyl).

Preferably, X is —I or —NR³R⁴, wherein R³ and R⁴ are independently of one another selected from —H, -methyl and -ethyl, wherein -methyl and -ethyl is optionally substituted with one or more —F (═—C₁-C₆-fluoroalkyl).

Preferably, X is —NR³R⁴, wherein R³ and R⁴ together with the nitrogen atom to which they are attached form a three, four, five, six, or seven membered heterocycloalkyl- or heteroaryl-ring, in each case independently unsubstituted or substituted; preferably R³ and R⁴ together with the nitrogen atom to which they are attached form a five membered heterocycloalkyl- or heteroaryl-ring, in each case independently unsubstituted or substituted; more preferably R³ and R⁴ together with the nitrogen atom to which they are attached form a pyrrolidine ring, piperidine ring, morpholine ring, piperazine ring, pyrrole ring, or imidazole ring, in each case independently unsubstituted or substituted with one or more —F.

In preferred embodiments,
(i) R³ and R⁴ are both —H; or
(ii) one of R³ and R⁴ is —H, whereas the other of R³ and R⁴ is —H; or
(iii) R³ and R⁴ are both ≠—H.

In a preferred embodiment, X is —NH₂.

In another preferred embodiment, X is selected from the group consisting of —NHCH₃, —NHCH₂CH₃, —N(CH₃)₂, —NH—CH₂—CH₂F, or —NH—CH₂—CHF₂.

In a particularly preferred embodiment, the dextrorphan-derivative according to the invention has a stereochemistry according to general formula (II):

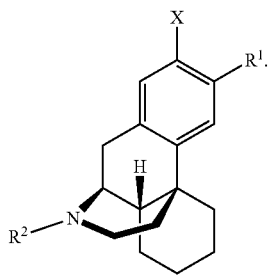

(II)

Preferred representatives are depicted here below:

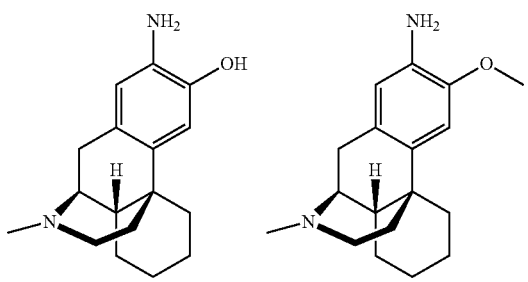

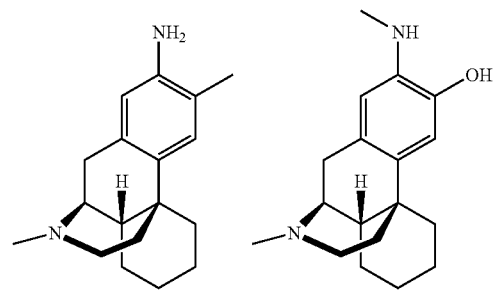

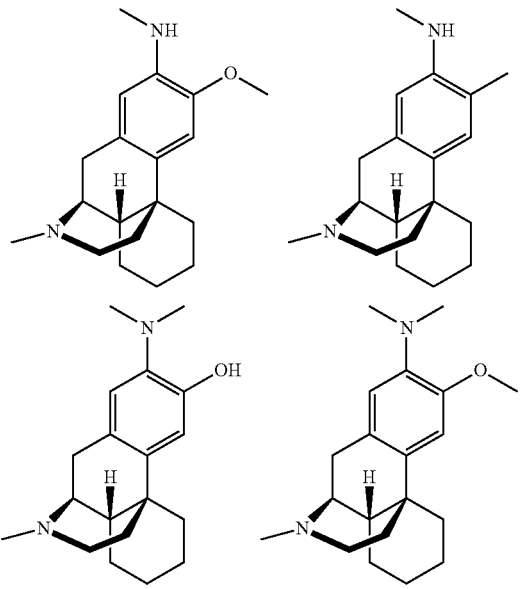

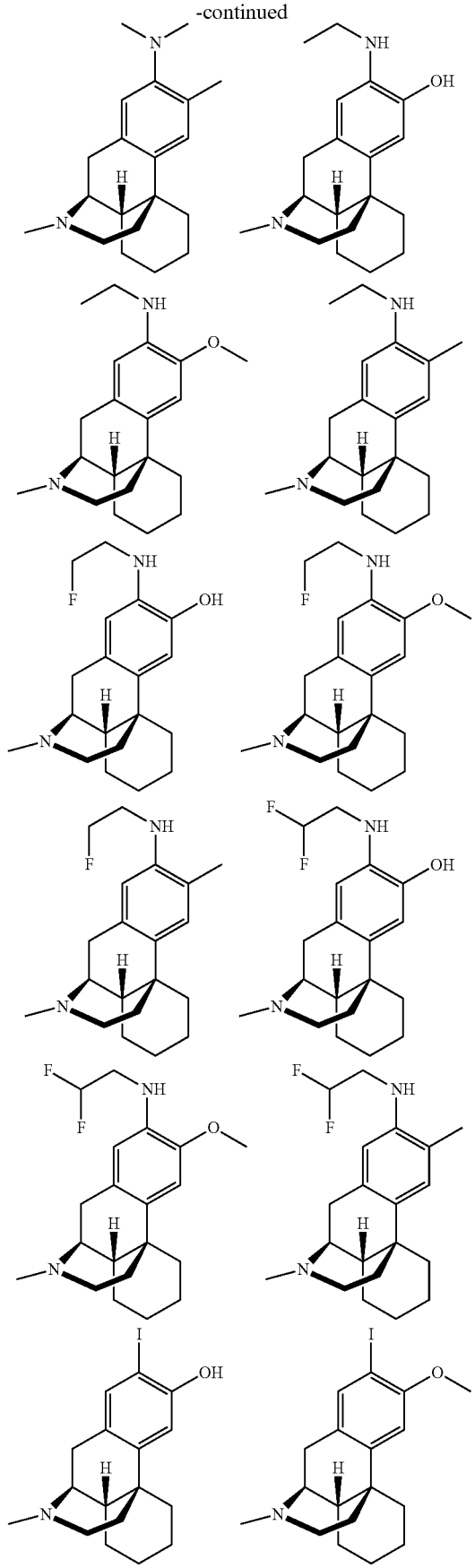
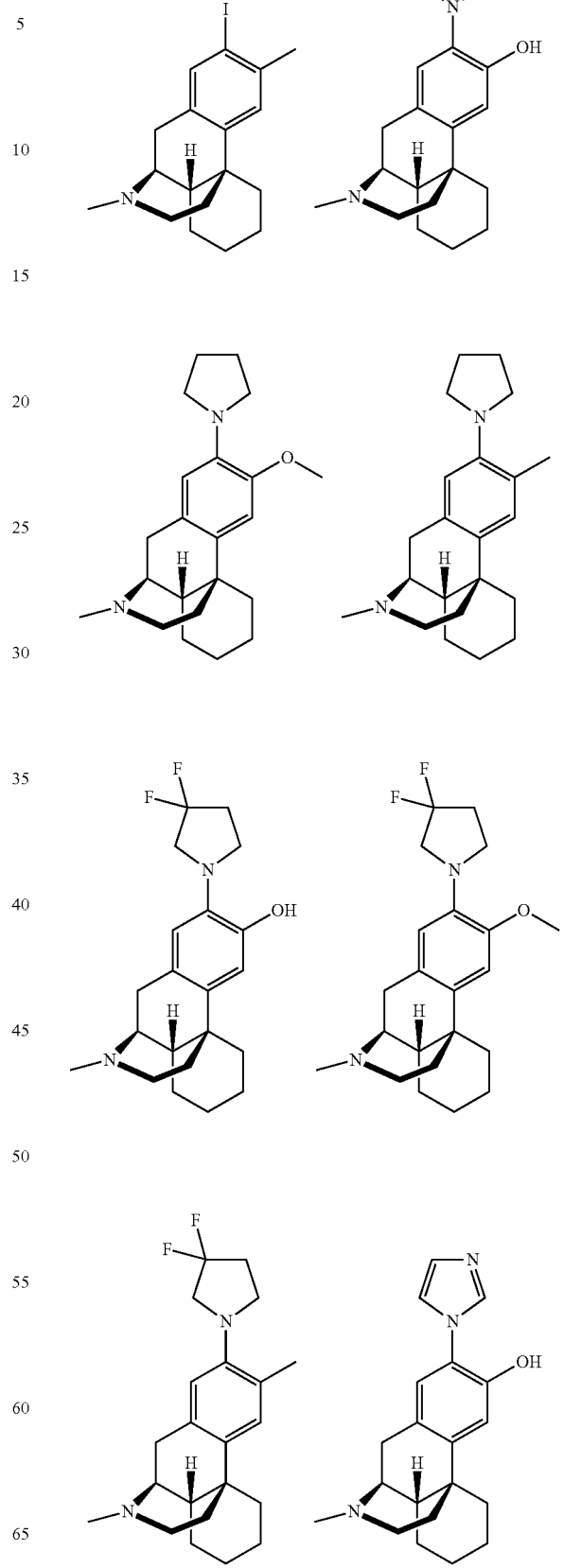

-continued

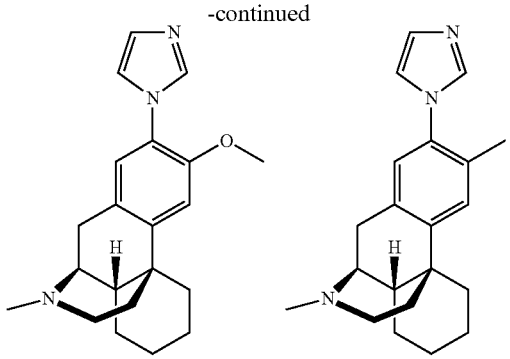

The above compounds usually rotate polarized light in (+)-direction (dextrorotatory) and the chiral centers usually have S-configuration according to CIP-nomenclature, although this may of course change depending upon the substituents.

Thus, particularly preferably, the dextrorphan-derivative is a (+)-dextrorphan-derivative selected from the group consisting of
(+)-2-amino-17-methyl-9α,13α,14α-morphinan-3-ol;
(+)-2-amino-3-methoxy-17-methyl-9α,13α,14α-morphinan;
(+)-2-amino-3-methyl-17-methyl-9α,13α,14α-morphinan;
(+)-2-methylamino-17-methyl-9α,13α,14α-morphinan-3-ol;
(+)-2-methylamino-3-methoxy-17-methyl-9α,13α,14α-morphinan;
(+)-2-methylamino-3-methyl-17-methyl-9α,13α,14α-morphinan;
(+)-2,2-dimethylamino-17-methyl-9α,13α,14α-morphinan-3-ol;
(+)-2,2-dimethylamino-3-methoxy-17-methyl-9α,13α,14α-morphinan;
(+)-2,2-dimethylamino-3-methyl-17-methyl-9α,13α,14α-morphinan;
(+)-2-ethylamino-17-methyl-9α,13α,14α-morphinan-3-ol;
(+)-2-ethylamino-3-methoxy-17-methyl-9α,13α,14α-morphinan;
(+)-2-ethylamino-3-methyl-17-methyl-9α,13α,14α-morphinan;
(+)-2-(2-fluoro-ethyl)amino-17-methyl-9α,13α,14α-morphinan-3-ol;
(+)-2-(2-fluoro-ethyl)amino-3-methoxy-17-methyl-9α,13α,14α-morphinan;
(+)-2-(2-fluoro-ethyl)amino-3-methyl-17-methyl-9α,13α,14α-morphinan;
(+)-2-(2,2-difluoro-ethyl)amino-17-methyl-9α,13α,14α-morphinan-3-ol;
(+)-2-(2,2-difluoro-ethyl)amino-3-methoxy-17-methyl-9α,13α,14α-morphinan;
(+)-2-(2,2-difluoro-ethyl)amino-3-methyl-17-methyl-9α,13α,14α-morphinan;
(+)-2-iodo-17-methyl-9α,13α,14α-morphinan-3-ol;
(+)-2-iodo-3-methoxy-17-methyl-9α,13α,14α-morphinan;
(+)-2-iodo-3-methyl-17-methyl-9α,13α,14α-morphinan;
(+)-2-(1-pyrrolidyl)-17-methyl-9α,13α,14α-morphinan-3-ol;
(+)-2-(1-pyrrolidyl)-3-methoxy-17-methyl-9α,13α,14α-morphinan;
(+)-2-(1-pyrrolidyl)-3-methyl-17-methyl-9α,13α,14α-morphinan;
(+)-2-(1-imidazolyl)-17-methyl-9α,13α,14α-morphinan-3-ol;
(+)-2-(1-imidazolyl)-3-methoxy-17-methyl-9α,13α,14α-morphinan;
(+)-2-(1-imidazolyl)-3-methyl-17-methyl-9α,13α,14α-morphinan;
or the physiologically acceptable salt and/or stereoisomer thereof, including mixtures thereof in all ratios.

Particularly preferred are the hydrochloride salts and the hydrobromide salts (i.e. acid addition salts).

The above compounds can be synthesized by standard derivatization of commercially available building blocks. In particular, commercially available are Dextromethorphan (i.e., (+)-3-methoxy-17-methyl-(9α,13α,14α)-morphinan, wherein $R^1$=—$OCH_3$, $R^2$=—$CH_3$); Dimemorphan (i.e. (+)-3-methyl-17-methyl-(9α,13α,14α)-morphinan, wherein $R^1$=—$CH_3$, $R^2$=—$CH_3$); Dextrorphan (i.e., (+)-17-methyl-9α,13α,14α-morphinan-3-ol, wherein $R^1$=—OH, $R^2$=—$CH_3$); 3-Hydroxymorphinan (i.e., (+)-9α,13α,14α-morphinan-3-ol, wherein $R^1$=—OH, $R^2$=—H); and 3-Methoxymorphinan (i.e., (+)-3-methoxy-(9α,13α,14α)-morphinan, wherein $R^1$=—$OCH_3$, $R^2$=—H). By standard derivatization, derivatives of these morphinans can be obtained. As far as standard derivatization reactions are concerned it can be referred to e.g. R. Larock, Comprehensive Organic Transformations: A Guide to Functional Group Preparations, Wiley-VCH, New York; and *Houben-Weyl Methods of Organic Chemistry*, Thieme, Stuttgart.

The invention also relates to mixtures of the dextrorphan-derivatives according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals, which occur more than once, their meanings are independent of one another.

In the dextrorphan-derivatives according to general formula (I), $R^0$ is in each case independently selected from —$C_1$-$C_6$-alkyl, -aryl, -heteroaryl, —$C_1$-$C_6$-alkyl-aryl or —$C_1$-$C_6$-alkyl-heteroaryl, in each case independently unsubstituted or substituted.

For the purpose of the specification, "—$C_1$-$C_6$-alkyl" means alkyl that is unbranched (linear) or branched, and has 1, 2, 3, 4, 5, or 6 C atoms, preferably -methyl, -ethyl, -propyl, -isopropyl, -butyl, -isobutyl, -sec-butyl, -tert-butyl, -pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted —$C_1$-$C_6$-alkyl include but are not limited to —$C_1$-$C_6$-alkyl-$CO_2H$, —$C_1$-$C_6$-alkyl-F, —$C_1$-$C_6$-alkyl-Cl, —$C_1$-$C_6$-alkyl-OH, —$C_1$-$C_6$-alkyl-O—$C_1$-$C_6$-alkyl and the like.

For the purpose of the specification, "aryl" denotes -phenyl, -naphthyl or -biphenyl.

For the purpose of the specification, "heterocycloalkyl" denotes an aliphatic monocyclic group, or a bicyclic group, each group containing from 4 to 11 ring members and from 1 to 5 hetero atoms selected from nitrogen, oxygen and sulphur. Preferred "heterocycloalkyl" includes piperidine, piperazine, morpholine, and pyrrolidine.

For the purpose of the specification, "heteroaryl" denotes an aromatic monocyclic group, or a bicyclic group in which at least one of the rings is aromatic, each group containing from 5 to 11 ring members and from 1 to 5 hetero atoms selected from nitrogen, oxygen and sulphur. A preferred heteroaryl is imidazole.

For the purpose of the specification, substituents of —$C_1$-$C_6$-alkyl, -heterocycloalkyl, -aryl, -heteroaryl, —$C_1$-$C_6$-alkyl-aryl or —$C_1$-$C_6$-alkyl-heteroaryl include one or more substituents independently of one another selected from -halogen (preferably —F), —$C_1$-$C_6$-alkyl, —$C_1$-$C_6$-alkoxy, hydroxy, mercapto, —$C_1$-$C_6$-alkylthio, -cyano, -amino (optionally substituted by one or two —$C_1$-$C_6$-alkyl), -nitro, -carboxy, —$C_1$-$C_6$-alkoxycarbonyl, -aminocarbonyl (optionally substituted by one or two —$C_1$-$C_6$-alkyl) or -carbamoyl, or —O—C(=O)—O—$C_1$-$C_6$-alkyl, enantiomers and diastereoisomers thereof, and addition salts thereof with a pharmaceutically acceptable acid or base.

Particularly preferred substituents of —$C_1$-$C_6$-alkyl are one or more —F. Preferred —$C_1$-$C_6$-fluoroalkyl groups include but are not limited to —$CH_2F$, —$CHF_2$, —$CF_3$, —$CH_2CH_2F$, —$CHFCH_3$, —$CHFCH_2F$, —$CF_2CH_3$, —$CH_2CHF_2$, —$CHFCHF_2$, —$CF_2CH_2F$, —$CH_2CF_3$, —$CHFCF_3$, $CF_2CHF_2$, and —$CF_2CF_3$.

The dextrorphan-derivatives have chiral centers and can therefore occur in various stereoisomeric forms. The general formula (I) encompasses all these forms.

The dextrorphan-derivatives according to the invention and also the starting materials for their preparation are prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the dextrorphan-derivatives according to the invention.

The starting compounds are generally known. If they are novel, however, they can be prepared by methods known per se.

The dextrorphan-derivatives according to the invention can be used in their final non-salt form. On the other hand, the invention also encompasses the use of these dextrorphan-derivatives in the form of their pharmaceutically acceptable salts, which can be derived from various organic and inorganic acids and bases by procedures known in the art. Pharmaceutically acceptable salt forms of the dextrorphan-derivatives are for the most part prepared by conventional methods. If the dextrorphan-derivative contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the dextrorphan-derivatives are likewise included.

In the case of certain dextrorphan-derivatives, acid-addition salts can be formed by treating the dextrorphan-derivatives with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the dextrorphan-derivatives include, but are not limited to acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, and phthalate.

Furthermore, the base salts of the dextrorphan-derivatives according to the invention include, but are not limited to aluminium, ammonium, calcium, copper, iron(III), iron(II), lithium, magnesium, manganese(III), manganese(II), potassium, sodium and zinc salts, but this is not intended to represent a restriction. Salts of the dextrorphan-derivatives which are derived from pharmaceutically acceptable organic non-toxic bases include, but are not limited to salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine).

The dextrorphan-derivatives of the invention typically contain basic nitrogen-containing groups that can be quaternized using agents such as —$C_1$-$C_4$-alkyl halides, for example -methyl, -ethyl, -isopropyl and -tert-butyl, -chloride, -bromide and -iodide; -di($C_1$-$C_4$)alkyl sulfates, for example -dimethyl, -diethyl and -diamyl sulfate; —($C_{10}$-$C_{18}$)alkyl halides, for example -decyl, -dodecyl, -lauryl, -myristyl-and stearyl chloride, bromide and iodide; and -aryl($C_1$-$C_4$)alkyl halides, for example -benzyl chloride and -phenethyl bromide. Both water- and oil-soluble dextrorphan-derivatives according to the invention can be prepared using such salts.

The above-mentioned pharmaceutical salts which are preferred include, but are not limited to acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine. The hydrochloride, hydrobromide and citrate are preferred.

The acid-addition salts of basic dextrorphan-derivatives are prepared by bringing the free base form into contact with a sufficient amount of the desired acid, causing the formation of the salt in a conventional manner. The free base can be regenerated by bringing the salt form into contact with a base and isolating the free base in a conventional manner.

The free base forms differ in a certain respect from the corresponding salt forms thereof with respect to certain physical properties, such as solubility in polar solvents; for the purposes of the invention, however, the salts otherwise correspond to the respective free base forms thereof.

The pharmaceutically acceptable base-addition salts of the dextrorphan-derivatives are preferably formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic dextrorphan-derivatives according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a dextrorphan-derivative according to the invention contains more than one group which is capable of forming pharmaceutically acceptable salts of this type, the invention also encompasses multiple salts. Typical multiple salt forms include, but are not limited to bitartrate, diacetate, difumarate, dimeglumine, diphosphate, disodium, dihydrobromide, trihydrobromide, dihydrochloride, and trihydrochloride.

Accordingly, the expression "pharmaceutically acceptable salt" for the purpose of the specification means an active ingredient which comprises a dextrorphan-derivative in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The dextrorphan-derivatives according to the invention are chiral owing to their molecular structure and may accordingly occur in various enantiomeric forms. They therefore exist in racemic or in optically active form. Since the pharmaceutical activity of the racemates or stereoisomers of the dextrorphan-derivatives according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilized on silica gel). Suitable eluents for this purpose are aqueous or alcoholic solvent mixtures, such as, for example, hexane/isopropanol/acetonitrile, for example in the ratio 82:15:3.

Another aspect of the invention relates to the dextrorphan-derivatives according to the invention as medicaments and/or medicament active ingredients, preferably for use in the treatment and/or prophylaxis of diseases or conditions selected from insulin-dependent diabetes mellitus, non-insulin-dependent diabetes mellitus; obesity; neuropathy and/or nephropathy, preferably diabetic nephropathy; cancer (in particular neuroendocrine tumors, pancreatic ductal carcinoma, breast cancer, ovarian cancer and glioma in which expression of NMDA receptors was shown to be expressed or correlated with a bad prognosis) (Li & Hanahan in Cell 2013, 153: 86-100), coronary heart disease and stroke as well as diabetic long-term complications (such as diabetic nephropathy, diabetic neuropathy diabetic retinopathy, stroke, myocardial infarction, etc.).

Another aspect of the invention relates to the use of the dextrorphan-derivatives according to the invention for the preparation of a pharmaceutical composition or pharmaceutical dosage form for the treatment and/or prophylaxis of the said diseases or conditions.

Another aspect of the invention relates to a method for the treatment and/or prophylaxis of said diseases or conditions which comprises the administration of an effective amount of one or more dextrorphan-derivatives according to the invention to a subject in need of such an administration.

The dextrorphan-derivatives according to the invention are not only useful for the treatment of insulin-dependent diabetes mellitus, but also for the treatment of non-insulin-dependent diabetes mellitus. This is because patients with non-insulin-dependent diabetes mellitus do also profit from beta-cell-stimulating therapies. As a matter of fact, the World Health Organization (WHO) placed the oral antidiabetic drug glibenclamide in their 17th edition of *Essential Medicine* in category 18.5, *Insulin and other medicines used for diabetes*. Glibenclamide stimulates insulin secretion from pancreatic islets of non-insulin-dependent diabetic patients, in particular type II diabetics. However, since glibenclamide stimulates basal insulin secretion from pancreatic islets to a large extent, hypoglycemic adverse events are encountered by this drug. In contrast to glibenclamide, however, the dextrorphan-derivatives according to the invention such as dextrorphan stimulate basal insulin secretion from pancreatic islets to a lesser extent. Thus, the dextrorphan-derivatives according to the invention likely have lesser hypoglycemic adverse effects compared to glibenclamide.

The dextrorphan-derivatives according to the invention are useful for treating diabetes mellitus type 2; particularly in overweight patients, when dietary management and exercise alone does not result in adequate glycemic control. The dextrorphan-derivatives may be used as monotherapy or in combination with other oral antidiabetic agents such as metformin, DPP-4 inhibitors (e.g. sitagliptin, vildagliptin), SGLT-2 inhibitors (e. g. empagliflozin, dapagliflozin), insulin sensitizers (e.g. pioglitazone, rosiglitazone), or with insulin and incretin-like drugs (e.g. exendin-4, liraglutide). The dextrorphan-derivatives might be orally applied or injected.

The host or patient may belong to any mammal species, for example a primate species, particularly humans; rodents, including mice, rats and hamsters; rabbits; horses, pigs, cows, dogs, cats, etc. Animal models are of interest for experimental investigations, where they provide a model for the treatment of a human disease.

The dextrorphan-derivatives according to the invention also mean the physiologically acceptable derivatives and solvates.

The invention also relates to the stereoisomers and the hydrates and solvates of these dextrorphan-derivatives. Solvates of the dextrorphan-derivatives include adductions of inert solvent molecules onto the dextrorphan-derivatives which form owing to their mutual attractive force. Solvates are, for example, mono- or dihydrates or alcoholates.

The dextrorphan-derivatives include the physiologically acceptable salts of the dextrorphan-derivatives according to the invention and also the prodrugs thereof.

Prodrugs mean dextrorphan-derivatives which have been modified, with, for example, alkyl or acyl groups, sugars or oligopeptides and which are rapidly cleaved in the organism to form the active dextrorphan-derivatives according to the invention. These also include biodegradable polymer derivatives of the dextrorphan-derivatives according to the invention.

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence: improved treatment, healing, prevention or elimination of a disease, syndrome, condition, complaint, disorder or prevention of side effects or also the reduction in the progress of a disease, condition, disorder or side effects or also the reduction in the progress of a disease, condition or disorder. The expression "therapeutically effective amount" also encompasses the amounts which are effective for increasing normal physiological function.

The invention furthermore relates to the use of the dextrorphan-derivatives and/or physiologically acceptable salts thereof for the preparation of medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one dextrorphan-derivative according to the invention and/or physiologically acceptable salts and stereoisomers thereof, including mixtures thereof in all ratios, and optionally excipients and/or adjuvants.

Pharmaceutical compositions can be administered in the form of pharmaceutical dosage forms which comprise a predetermined amount of active ingredient per pharmaceutical dosage forms. Such a unit can comprise, for example, 1 mg to 2 g, preferably 30 mg to 1 g, particularly preferably 50 mg to 1000 mg, of a dextrorphan-derivative according to the invention, depending on the disease condition treated, the method of administration and the age, weight and condition of the patient, or pharmaceutical compositions can be administered in the form of pharmaceutical dosage forms which comprise a predetermined amount of dextrorphan-derivative per pharmaceutical dosage forms. Preferred pharmaceutical dosage forms pharmaceutical compositions are those which comprise a daily dose or part-dose, as indicated above, or a corresponding fraction thereof of an active ingredient. Furthermore, pharmaceutical compositions of this type can be prepared using a process which is generally known in the pharmaceutical art. For comparison, the anti-diabetic drug metformin is currently administered in units of 500 mg to 1 g.

Pharmaceutical compositions can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such pharmaceutical compositions can be prepared using all processes known in the pharmaceutical art by, for example, combining the active ingredient with the excipient(s) or adjuvant(s).

Pharmaceutical compositions adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the dextrorphan-derivative can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavor, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubilizer, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The dextrorphan-derivatives according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different pharmaceutical dosage forms.

Oral liquids, such as, for example, solution, syrups and elixirs, can be prepared in the form of pharmaceutical dosage forms so that a given quantity comprises a pre specified amount of the dextrorphan-derivatives. Syrups can be prepared by dissolving the dextrorphan-derivatives in an aqueous solution with a suitable flavour, while elixirs are prepared using a non-toxic alcoholic vehicle. Suspensions can be formulated by dispersion of the dextrorphan-derivatives in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The pharmaceutical dosage forms pharmaceutical compositions for oral administration can, if desired, be encapsulated in microcapsules. The pharmaceutical composition can also be prepared in such a way that the release is extended or retarded, such as, for example, by coating or embedding of particulate material in polymers, wax and the like.

The dextrorphan-derivatives according to the invention and salts, solvates and derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The dextrorphan-derivatives according to the invention and the salts, solvates and derivatives thereof can also be delivered using monoclonal antibodies as individual carriers to which the dextrorphan-derivatives are coupled. The dextrorphan-derivatives can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The dextrorphan-derivatives may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical compositions adapted for transdermal administration can be administered as independent plasters for extended, close contact with the epidermis of the recipient. Thus, for example, the dextrorphan-derivatives can be delivered from the plaster by iontophoresis.

Pharmaceutical compositions adapted for topical administration can be formulated as ointments, creams, suspensions, lotions, powders, solutions, pastes, gels, sprays, aerosols or oils.

Pharmaceutical compositions adapted for topical application in the mouth encompass lozenges, pastilles and mouthwashes.

Pharmaceutical compositions adapted for rectal administration can be administered in the form of suppositories or enemas.

Pharmaceutical compositions adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable pharmaceutical compositions for administration as nasal spray or nose drops with a liquid as carrier substance encompass solutions of the dextrorphan-derivatives in water or oil.

Pharmaceutical compositions adapted for administration by inhalation encompass finely particulate dusts or mists, which can be generated by various types of pressurized dispensers with aerosols, nebulizers or insufflators.

Pharmaceutical compositions adapted for vaginal administration can be administered as pessaries, tampons, creams, gels, pastes, foams or spray pharmaceutical compositions.

Pharmaceutical compositions adapted for parenteral administration include aqueous and non-aqueous sterile injection solutions comprising antioxidants, buffers, bacteriostatics and solutes, by means of which the pharmaceutical composition is rendered isotonic with the blood of the recipient to be treated; and aqueous and non-aqueous sterile suspensions, which may comprise suspension media and thickeners. The pharmaceutical compositions can be administered in single-dose or multidose containers, for example sealed ampoules and vials, and stored in freeze-dried (lyophilized) state, so that only the addition of the sterile carrier liquid, for example water for injection purposes, immediately before use is necessary.

Injection solutions and suspensions prepared in accordance with the recipe can be prepared from sterile powders, granules and tablets.

Pharmaceutical compositions for parenteral administration are preferably administered by injection or infusion, preferably intravenously, intramuscularly, subcutaneously, or the like.

In addition to the above particularly mentioned constituents, the pharmaceutical compositions may also comprise other agents usual in the art with respect to the particular type of pharmaceutical composition; thus, for example, pharmaceutical compositions which are suitable for oral administration may comprise flavours.

A therapeutically effective amount of a dextrorphan-derivative of the invention depends on a number of factors, including, for example, the age and weight of the human or animal, the precise disease condition which requires treatment, and its severity, the nature of the pharmaceutical composition and the method of administration, and is ultimately determined by the treating physician or veterinarian. However, an effective amount of a dextrorphan-derivative according to the invention is generally in the range from 0.05 to 100 mg/kg of body weight of the recipient (mammal) per day and particularly typically in the range from 0.3 to 15 mg/kg of body weight per day. Thus, the actual amount per day for an adult mammal weighing 70 kg is usually between 20 mg and 1000 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the dextrorphan-derivative according to the invention per se. It can be assumed that similar doses are suitable for the treatment of other conditions mentioned above. For comparison, the daily dose of metformin used in type 2 diabetic patients is similarly 500 mg to 3 g.

In a particularly preferred embodiment, the dextrorphan-derivative according to the invention is administered once daily, or twice daily, or thrice daily, or four times daily, the individually administered dose per administration being within the range of 30±15 mg, or 60±15 mg, or 90±15 mg, or 120±15 mg, or 150±15 mg, or 180±15 mg, or 210±15 mg, or 240±15 mg, or 270±15 mg, or 300±15 mg, or 310±15 mg, or 340±15 mg, or 370±15 mg, or 400±15 mg, or 410±15 mg, or 440±15 mg, or 470±15 mg, or 500±15 mg, or 750±15 mg, or 1,000±15 mg.

In a preferred embodiment, particularly when the dextrorphan-derivative according to the invention is intended for administration over an extended period of time such as several months or years, it is preferred to initiate administration at a comparatively low daily dose and to consecutively, preferably steadily increase the daily dose over a titration period until the desired maximum daily dose has been reached (dose titration). Once the maximum daily dose has been reached, the titration period is terminated and continuous administration proceeds which may also include a subsequent reduction of the daily dose, if desired.

In the following embodiments, the daily dose of the dextrorphan-derivative is preferably administered on each day, independently of one another, all at once (once daily, sid), divided in two portions (twice daily, bid), divided in three portions (thrice daily), or divided in four portions (four times daily).

In a preferred embodiment, the dextrorphan-derivative is administered by injection twice daily, once daily or less frequently, e.g. once in a week, optionally in combination with other drugs, such as in combination with liraglutide, preferably once daily, or in combination with exendin-4, e.g. twice daily or only once in a week.

In a preferred embodiment, the titration regimen is biphasic, i.e. includes the administration of two different daily doses $d_1$ and $d_2$, wherein daily dose $d_1$ is administered during a first administration interval $a_1$, preferably on every day, and daily dose $d_2$ is administered during a second administration interval $a_2$, preferably on every day, which second administration interval $a_2$ follows the first administration interval $a_1$, and wherein daily dose $d_1$<daily dose $d_2$. Preferably, daily dose $d_2$ is the maximum daily dose to be finally administered, and daily dose $d_1$ is within the range of from 10 to 90 wt.-% of daily dose $d_2$, more preferably 20 to 80 wt.-%, still more preferably 30 to 70 wt.-%, and most preferably 40 to 60 wt.-% of daily dose $d_2$. Preferably, the first administration interval $a_1$ comprises at least 2 days, more preferably at least 4 days, still more preferably at least 7 days, yet more preferably at least 14 days, even more preferably at least 21 days, most preferably at least 28 days, and in particular at least 2 months. Preferably, the second administration interval $a_2$ comprises at least 2 days, more preferably at least 4 days, still more preferably at least 7 days, yet more preferably at least 14 days, even more preferably at least 21 days, most preferably at least 28 days, and in particular at least 2 months. Thus, according to this embodiment, the titration period comprises the first administration interval $a_1$.

In another preferred embodiment, the titration regimen is triphasic, i.e. includes the administration of three different daily doses $d_1$, $d_2$ and $d_3$, wherein daily dose $d_1$ is administered during a first administration interval $a_1$, preferably on every day, daily dose $d_2$ is administered during a second administration interval $a_2$, preferably on every day, which second administration interval $a_2$ follows the first administration interval $a_1$, and daily dose $d_3$ is administered during a third administration interval $a_3$, preferably on every day, which third administration interval $a_3$ follows the second administration interval $a_2$, and wherein daily dose $d_1$<daily dose $d_2$<daily dose $d_3$. Preferably, daily dose $d_3$ is the maximum daily dose to be finally administered; and daily dose $d_1$ is within the range of from 5 to 55 wt.-% of daily dose $d_3$, more preferably 10 to 50 wt.-%, still more preferably 15 to 45 wt.-%, and most preferably 20 to 40 wt.-% of daily dose $d_3$; and daily dose $d_2$ is within the range of from 45 to 95 wt.-% of daily dose $d_3$, more preferably 50 to 90 wt.-%, still more preferably 55 to 85 wt.-%, and most preferably 60 to 80 wt.-% of daily dose $d_3$. Preferably, the first administration interval $a_1$ comprises at least 2 days, more preferably at least 4 days, still more preferably at least 7 days, yet more preferably at least 14 days, even more preferably at least 21 days, most preferably at least 28 days, and in particular at least 2 months. Preferably, the second administration interval $a_2$ comprises at least 2 days, more preferably at least 4 days, still more preferably at least 7 days, yet more preferably at least 14 days, even more preferably at least 21 days, most preferably at least 28 days, and in particular at least 2 months. Preferably, the third administration interval $a_3$ comprises at least 2 days, more preferably at least 4 days, still more preferably at least 7 days, yet more preferably at least 14 days, even more preferably at least 21 days, most preferably at least 28 days, and in particular at least 2 months. Thus, according to this embodiment, the titration period comprises the first administration interval $a_1$ as well as the second administration interval $a_2$.

In a preferred embodiment, the titration regimen is multiphasic, i.e. includes the administration of a multitude of different daily doses $d_1$, $d_2$, $d_3$, ... $d_n$, wherein daily dose $d_1$ is administered during a first administration interval $a_1$, preferably on every day, daily dose $d_2$ is administered during a second administration interval $a_2$, preferably on every day, which second administration interval $a_2$ follows the first administration interval $a_1$, daily dose $d_3$ is administered during a third administration interval $a_3$, preferably on every day, which third administration interval $a_3$ follows the second administration interval $a_2$, and so on, until daily dose $d_n$ is administered during a final administration interval $a_n$ of the titration period, preferably on every day, and wherein daily dose $d_1$<daily dose $d_2$<daily dose $d_3$< ... <$d_n$. For example, daily dose $d_1$ may amount to 120 mg of the dextrorphan-derivative. Daily dose $d_1$ may be administered all at once (once daily, sid), divided in two portions each amounting to 60 mg (twice daily, bid), divided in three portions each amounting to 40 mg (thrice daily), or divided in four portions each amounting to 30 mg (four times daily). During the titration phase, the daily dose $d_1$ may be increased up to a maximum daily dose $d_n$ of e.g. 960 mg. For example, during a titration phase of four weeks the daily dose may be increased by 30 mg to 60 mg, e.g. every three days, unless the patient reports complete therapeutic effect, side effects that interfere with daily activities, or unless the maximum daily dose $d_n$ is reached. Thus, the further increase of the daily dose during the titration phase depends on the perception of the patient. In the following administration interval (maintenance phase), the highest well-tolerated daily dose can be maintained at a constant level.

The invention furthermore relates to medicaments comprising at least one dextrorphan-derivative according to the invention and/or physiologically acceptable salts and stereoisomers thereof, including mixtures thereof in all ratios, and at least one further medicament active ingredient.

The invention also relates to a set (kit) comprising separate packs of (a) an effective amount of a dextrorphan-derivative according to the invention and/or physiologically acceptable salts and stereoisomers thereof, including mixtures thereof in all ratios; and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or physiologically acceptable salts and stereoisomers thereof, including mixtures thereof in all ratios, and an effective amount of a further active ingredient in dissolved or lyophilised form. Preferably, said further active ingredient is metformin or a physiologically acceptable salt thereof.

The dextrorphan-derivatives are suitable as pharmaceutical active ingredients for mammals, in particular for humans, in the treatment or prophylaxis of diabetes type 1, diabetes type 2; latent autoimmune diabetes in adults (LADA), obesity; neuropathy and/or nephropathy, stroke, cardiovascular diseases (such as myocardial infarction), hypertension, preferably diabetic nephropathy and neuropathy; and cancer.

The invention thus relates to the use of dextrorphan-derivatives and to physiologically acceptable derivatives, solvates and stereoisomers, including mixtures thereof in all ratios, for the preparation of a medicament for the treatment or prophylaxis of diabetes type 1, diabetes type 2; obesity; neuropathy and/or nephropathy, preferably diabetic nephropathy; and cancer.

The dextrorphan-derivatives of the invention can be used as prophylactics or therapeutic agents for treating diseases or disorders mediated by deficient levels of GLP-1 activity or which can be treated by activating TGR5 including, but not limited to, diabetes mellitus, impaired glucose tolerance (IGT), impaired fasting glucose (IFG) and elevated levels of glycated hemoglobin (HbA1c) as well as other diseases and disorders such as those discussed below. Furthermore, the dextrorphan-derivatives of the invention can be also used to prevent the progression of the borderline type, IGT and IFG to diabetes mellitus.

The dextrorphan-derivatives of the invention can be also used as prophylactics or therapeutic agents of diabetic complications such as, but not limited to, neuropathy, nephropathy, preferably diabetic nephropathy, retinopathy, cataract, macroangiopathy, cerebrovascular disease (e.g. stroke), cardiovascular disease (e.g. myocardial infarction), endothelial dysfunction, hypertension, diabetic foot, osteopenia, diabetic hyperosmolar coma, infectious diseases (e.g., respiratory infection, urinary tract infection, gastrointestinal tract infection, dermal soft tissue infection, lower limb infection etc.), diabetic gangrene, xerostomia, decreased sense of hearing, peripheral circulatory disturbance, cancer, etc.

The dextrorphan-derivatives of the invention can be also used as prophylactics or therapeutic agents in the treatment of diseases and disorders such as, but not limited to, obesity, metabolic syndrome (syndrome X), hypertension, hyperinsulinemia, hypoinsulinemia, hyperinsulinemia-induced sensory disorder, hypoinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis, nephrotic syndrome, hypertensive nephrosclerosis, terminal renal disorder etc.), cardiovascular disease (e.g. myocardial infarction), angina pectoris, and cerebrovascular disease (e.g., cerebral infarction, cerebral apoplexy).

The dextrorphan-derivatives of the invention can also be used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, sudden infant death syndrome (SIDS), and the like.

The dextrorphan-derivatives of the invention can be used in combination with one or more additional drugs such as described below. The dose of the second drug can be appropriately selected based on a clinically employed dose. The proportion of the dextrorphan-derivatives and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the dextrorphan-derivatives.

The second compound of the pharmaceutical combination, pharmaceutical composition or dosing regimen preferably has complementary activities to the dextrorphan-derivative such that they do not adversely affect each other. Such drugs are suitably present in combination in amounts that are effective for the purpose intended. Accordingly, another aspect of the invention provides a composition comprising a dextrorphan-derivative according to the invention, or a solvate, metabolite, or pharmaceutically acceptable salt or prodrug thereof, in combination with a second drug, such as described herein.

The dextrorphan-derivative and the additional pharmaceutically active agent(s) may be administered together in a unitary pharmaceutical composition or separately and, when administered separately this may occur simultaneously or sequentially in any order. Such sequential administration may be close in time or remote in time. The amounts of the dextrorphan-derivative and the second agent(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are (1) co-formulated and administered or delivered simultaneously in a combined, unit dosage pharmaceutical composition; (2) delivered by alternation or in parallel as separate pharmaceutical compositions; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The dextrorphan-derivatives of the invention can be used, for example in combination with additional drug(s) such as a therapeutic agent for diabetes mellitus, and/or a therapeutic agent for diabetic complications, as defined above.

Examples of known therapeutic agents for diabetes mellitus which can be used in combination with a dextrorphan-derivative include insulin preparations (e.g., animal insulin preparations extracted from the bovine or swine pancreas; human insulin preparations synthesized by a genetic engineering technique using Escherichia coli or a yeast), a fragment of insulin or derivatives thereof (e.g., INS-i), agents for improving insulin sensitivity (e.g., pioglitazone hydrochloride, troglitazone, rosiglitazone or its maleate, GI-262570, JTT-50 1, MCC-555, YM-440, KRP-297, CS-Oil, FK-614), alpha-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chiorpropamide, tolazamide, acetohexamide, glyclopyramide, glimepiride, glipizide, glybuzole), repaglinide, nateglinide, mitiglinide or its calcium salt hydrate, GLP-1J, exendin-4, liraglutide and other incretin-based drugs, dipeptidylpeptidase IV inhibitors (e.g., NVP-DPP-278, PT-100, sitagliptin, vildagliptin), beta-3 agonists (e.g., CL-3 16243, SR-58611-A, UL-TG-307, SB-226552, AJ-9677, BMS196085, AZ-40140 etc.), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T1095, canagliflozin, dapagliflozin, empagliflozin), and the like.

Examples of known therapeutic agents for diabetic complications include aldose reductase inhibitors (e.g., tolrestat, epairestat, zenarestat, zopobestat, minairestat, fidarestat (SNK-860), CT-i 12), neurotrophic factors (e.g., NGF, NT-3, BDNF), neurotrophic factor production secretion promoters, PKC inhibitors (e.g., LY-333531), AGE inhibitors (e.g., ALT946, pimagedine, pyratoxathine, Nphenacylthiazolium bromide (ALT766), EXO-226), active oxygen scavengers (e.g., thioctic acid), and cerebral vasodilators (e.g., tiapuride, mexiletine).

The dextrorphan-derivatives of the invention can also be used, for example in combination with antihyperlipidemic agents. Epidemiological evidence has firmly established hyperlipidemia as a primary risk factor in causing cardiovascular disease (CVD) due to atherosclerosis. In recent years, emphasis has been placed on lowering plasma cholesterol levels, and low density lipoprotein cholesterol in particular, as an essential step in prevention of CVD.

Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance. Examples of antihyperlipidemic agents include statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

The dextrorphan-derivatives of the invention can also be used, for example in combination with hypotensive agents. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension. Examples of hypotensive agents include angiotensin converting enzyme inhibitors (e.g., captopril, enalapril, delapril), angiotensin II antagonists (e.g., candesartan cilexetil, losartan, eprosartan, valsantan, termisartan, irbesartan, tasosartan), calcium antagonists (e.g., manidipine, nifedipine, nicardipine, amlodipine, efonidipine), and clonidine.

The dextrorphan-derivatives of the invention can be used in combination with anti-obesity agents. The term "obesity" implies an excess of adipose tissue. Obesity is a well-known risk factor for the development of many very common diseases such as diabetes, atherosclerosis, and hypertension. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding center that stimulates eating, and the satiety center modulates this process by sending inhibitory impulses to the feeding center. Several regulatory processes may influence these hypothalamic centers. The satiety center may be activated by increases in plasma glucose and/or insulin that follow a meal. Examples of anti-obesity agents include anti-obesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists (e.g., CL-3 16243, SR-5861 1-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-1 5849).

The dextrorphan-derivatives of the invention can be used in combination with anti-cancer agents. These include, but are not limited to, alkylating agents (e.g. cyclophosphamide, temozolomide, cisplatin), antimetabolites (e.g., 5-fluorouracil, capecitabine, cytarabine, gemcitabine, hydroxyurea, methotrexate, pemetrexed), anti-tumor antibiotics (e.g., doxorubicine, actinomycin-D, mitomycin-C), topoisomerase inhibitors (e.g., topotecan, irinotecan, etoposide, teniposide, mitoxantrone), mitotic inhibitors (e. g., paclitaxel, docetaxel, ixabepilone, vinblastine, vincristine, vinorelbine, estramustine),
tyrosine kinase inhibitors (e.g., imatinib, erlotinib),
corticosteroids (e.g., prednisone, methylprednisolone, dexamethasone),
L-asparaginase,
bortezomib, and
anti-angiogenesis drugs (e.g., bevacizumab).

For breast cancer treatment, the dextrorphan-derivatives are preferably combined with
surgery,
radiation therapy,
chemotherapy (e.g. with docetaxel, paclitaxel, cisplatin, carboplatin, vinorelbine, capecitabine, liposomal doxorubicin, gemcitabine, mitoxantrone, ixabepilone, albumin-bound paclitaxel or eribulin),
hormone therapy (e.g. toremifene, fulvestrant, letrozole, anastrozole or exemestane), targeted therapy (e.g. trastuzumab, pertuzumab, ado-trastuzumab emtansine or lapatinib), and/or
bone-directed therapy.

For pancreatic cancer treatment, the dextrorphan-derivatives are preferably combined with
surgery,
chemotherapy (e.g. gemcitabine, 5-FU, albumin-bound paclitaxel, erlotinib, capecitabine, leucovorin, irinotecan, oxaliplatin, cisplatin, paclitaxel, docetaxel, irinotecan liposome, doxorubicin, decarbazine, temozolomide, streptozocin, thalidomide),
radiation therapy,
hormone therapy (e.g. octreotide), and/or
targeted therapy (e.g erlotinib, sunitinib or everolimus).

For glioma treatment, the dextrorphan-derivatives are preferably combined with
surgery,
radiation therapy, and/or
chemotherapy (e.g. carmustine, temozolomide, procarbazine, lomustine or vincristine).

For ovarian cancer, the dextrorphan-derivatives are preferably combined with
surgery,
chemotherapy (e.g. cisplatin, carboplatin, paclitaxel, albumin-bound paclitaxel, altretamine, capecitabine, cyclophosphamide, etoposide, gemcitabine, ifosfamide, irinotecan, liposomal doxorubicin, melphalan, pemetrexed, tropotecan, vintorelbine or docetaxel),
radiation therapy,
hormone therapy (e.g. goserelin, leuprolide, aromatase, letrozole, anastrozole or exemestane), and/or
targeted therapy (e.g. bevacizumab or olaparib).

EXAMPLES

The following examples further illustrate the invention but are not to be construed as limiting its scope. The following examples shall illustrate that (i) the derivatives can be synthesized at a purity of around 90% or more, (ii) the derivatives increase glucose-stimulated insulin secretion from pancreatic islets, but have little effect on basal insulin secretion, showing that they are superior over sulfonlyureas as anti-diabetic drugs that also increase basal insulin release to a large extent and thus introduce hypoglycemia as life-threatening adverse event, (iii) the derivatives are capable to lower blood glucose excursions in a glucose tolerance test and thus have strong anti-diabetic properties, (iv) the derivatives access the cerebrospinal fluid to a significantly lesser extent compared to dextrorphan, and (v) probably resulting from their reduced blood brain permeability, the derivatives induce no or few coordination deficits as shown by a rotarod test, whereas the original compound dextrorphan does.

FIG. 1: General overview over the route for synthesizing exemplified dextrorphan-derivatives of the invention:

Example 1—Synthesis of (2) from (1)—Phenylether Cleavage 10 g (27 mmol) dextromethorphan (1) hydrobromide monohydrate was dissolved in 104 mL of 47% HBr in a sealed tube and stirred at 100° C. After 22 h, heating was stopped. The mixture was poured to ice water (200 mL). $K_2CO_3$ was added until pH=10. The mixture was extracted with dichloromethane (4×250 mL). The organic layer was dried over $MgSO_4$ and concentrated to dryness under reduced pressure. Yield of the desired product (2): 7.6 g (LC/MS purity >95%, NMR purity ~90%).

Example 2—Synthesis of (3) from (2)—Nitration 800 mg of (2) was dissolved in 7 mL formic acid at 0° C. (in ice bath over 40 min.) under $N_2$ atmosphere. 217 mg 90% $HNO_3$ was slowly dropped to the reaction mixture. After 30 min, the reaction mixture was diluted with dichloromethane (100 mL). Ice cold sat. $NaHCO_3$ was dropped to reaction mixture until pH=4-5. After separation, the aqueous layer was extracted with dichloromethane (2×100 mL) and chloroform (4×100 mL). The organic layers were combined, dried over $MgSO_4$ and concentrated to dryness. The product (3) was purified by flash chromatography ($H_2O$ (+0.1 HCl)/acetonitrile). Yield of the desired product (3): 300 mg (LC/MS purity >95%)

Example 3—Synthesis of (4) from (3)—Reduction 460 mg (1.52 mmol) of (3) was dissolved under $N_2$ atmosphere in methanol (8 mL). 260 μL conc. HCl (2 eq) and 40 mg Pd/C were added to mixture under $H_2$ atmosphere. After reaction and filtration, reaction mixture was concentrated under reduced pressure. Yield of desired product (4): 0.5 g solid (LCMS purity about 70%). The product (4) was purified by preparative HPLC (C18, $H_2O$/acetonitrile, 0.1% formic acid). Yield of the desired product (4): 40 mg solid (LC/MS purity >95%)

Example 4—Synthesis of (5) from (2)—Iodation 17.8 g (0.107 mol) KI and 17.8 g (0.070 mol) $I_2$ were added to water (1.4 L). The mixture was stirred at room temperature for 6 h. 2×7 g of (2) was dissolved in 2M NaOH (2×210 mL). Then water (700 mL) was added to the solution. The solution of $KI/I_2$ (2×0.6 L) were dropped into the solution of (2) at room temperature in 30 min. After the addition, the reaction mixture was stirred for 2 h. Then, the reaction mixture was stirred overnight and neutralized by the addition of 10% HCl. After filtration, solid was collected. The filtrate was extracted with chloroform (6×300 mL). Then, the aqueous layer was extracted with a mixture of isopropanol: chloroform 3:7 (3×200 mL). The collected solid was dissolved in methanol and diluted with chloroform. This mixture was washed with sat. $NaHCO_3$. After separation, it was combined with the organic layer and was dried and concentrated to dryness. Yield of desired product (5): 20.1 g solid (purity >95% LCMS).

Example 5—Synthesis of (6) from (5)—Protection by Benzylether 4 g (10.4 mmol) of (5) was dissolved in dry dimethylformamide (39 mL) at 0° C. (in ice bath over 40 min.) under $N_2$ atmosphere. 416 mg 60% NaH was added to reaction mixture at 0° C. portion wise. After 40 min, 1.7 g (10 mmol) benzyl bromide in dry dimethylformamide (1.5 mL) was dropped into reaction mixture at this temperature in 3 min. After addition, the reaction mixture was kept at 0° C. After 20 min, reaction was stopped. Reaction mixture was quenched with sat. $NH_4Cl$ and extracted with dichloromethane (4×100 mL). Organic layer was combined, dried with MgSO4 and concentrated to dryness. Yield of desired product (6): 5.2 g (82% LCMS). The product (6) was purified by flash chromatography (dichloromethane/methanol). Yield of the purified product (6): 3.79 g (purity >95% LCMS; >90% NMR).

Example 6—Synthesis of (7a) from (6)—Amination $K_2CO_3$ was dried under high vacuum. 0.9 g (1.9 mmol) of (6), 526 mg (3.8 mmol) dry $K_2CO_3$, 110 mg (0.57 mmol) CuI, 132 mg (1.14 mmol) L-proline were added to dry dimethylsulfoxide (3 mL) under $N_2$ atmosphere. 4 mL 2M methylamine in tetrahydrofurane was added to reaction mixture. After addition, reaction was heated to 90° C. After stirring overnight another 4 mL 2M methylamine in tetrahydrofurane were added. After stirring overnight, 11 mg CuI and 132 g L-proline in dimethylsulfoxide (0.5 mL) and 2 mL 2M methylamine in tetrahydrofurane were added to reaction mixture. Reaction mixture was heated to 100° C. The reaction mixture was cooled to room temperature and diluted with water (30 mL). The mixture was extracted with ethylacetate (6×50 mL) and chloroform (2×30 mL). After separation, organic layer was dried over $MgSO_4$ and concentrated to dryness. 1.2 g oil was obtained after 1 h high vacuum. Yield of desired product (7): 1.2 g (purity 57% LCMS). The product (7) was purified by flash chromatography ($H_2O$ (+0.1% formic acid)/acetonitrile).

Example 7—Synthesis of (8a) from (7a)—Deprotection by Benzylether Cleavage 400 mg of (7a) was dissolved in acetonitrile (2 mL). Then 1.5 mL of HBr (48%) was dropped to the solution. After addition, reaction mixture was heated to 80° C. After 24 h, another 1.8 mL of HBr (48%) was added to reaction mixture. After stirring overnight, another 1 mL of HBr (48%) was added to reaction mixture. Then, reaction was cooled to room temperature and stored at −20° C. After warmed to room temperature, reaction mixture was filtrated. Filtrate was concentrated to dryness. 700 mg mixture was obtained. LCMS showed about 40% product. After purification by prep. HPLC (C18, $H_2O$/acetonitrile, 0.1% formic acid), (8a) was dried by freeze-drying. 91 mg (8a) were obtained (purity over 95%, UHPLC, NMR).

Example 8—Synthesis of (7b) from (6)—Amination $K_2CO_3$ was dried under high vacuum. 0.9 g (1.9 mmol) of (6), 526 mg (3.8 mmol) dry $K_2CO_3$, 110 mg (0.57 mmol) CuI, 132 mg (1.14 mmol) L-proline were added to dry dimethylsulfoxide (3 mL). 4 mL 2M ethylamine in tetrahydrofurane was added to reaction mixture. After addition, reaction was heated to 90° C. After stirring overnight, another 4 mL 2M ethylamine in tetrahydrofurane were added to reaction and it was run another 24 h. Then, 0.1 g CuI and 0.132 g L-proline in dimethylsulfoxide (0.5 mL) and tetrahydrofurane (4 mL) were added to reaction mixture. The mixture was heated to 100° C. and stirred overnight. Reaction mixture was cooled to room temperature and diluted with water (30 mL). The mixture was extracted with ethylacetate (6×50 mL) and chloroform (2×30 mL). After separation, organic layer was dried over $MgSO_4$ and concentrated to dryness. 1.2 g oil was obtained after high vacuum. The yield of the desired product (7b) was 1.2 g (purity about 50% UHPLC). The product was purified by flash chromatography ($H_2O$ (+0.1 formic acid)/acetonitrile).

Example 9—Synthesis of (8b) from (7b)—Deprotection by Benzylether Cleavage 300 mg (0.768 mmol) of (7b) were dissolved in dry acetonitrile (3 mL). 2.6 mL of HBr (48%) was added and the reaction mixture was stirred at 80° C. After stirring overnight, another 0.3 mL of HBr (48%) was added to reaction mixture. After another 8 h, reaction was cooled to room temperature. After stirring overnight, the reaction mixture was filtrated. Filtrate cake was washed with acetonitrile. 400 mg solid was obtained (purity is about 55%). After purification by prep. HPLC ($C_{18}$, $H_2O$/acetonitrile, 0.1% formic acid), 86 mg of (8b) were obtained (purity over 95% UHPLC, NMR).

Example 10—Synthesis of (7c) from (6)—Amination $K_2CO_3$ was dry under high vacuum. 97 mg CuI and 117 mg L-proline were dissolved in dry dimethylsulfoxide (2 mL). After degassing with $N_2$, it has been stirred at room temperature for 10 min. Then 0.8 g (1.7 mmol) of (6) and 467 mg (1.7 mmol) dry $K_2CO_3$ were added to the mixture. 4 mL 2M dimethylamine in tetrahydrofurane was added to reaction mixture. After addition, reaction was heated to 90° C. After reaction for 72 h, the reaction was cooled to room temperature. A solution of 97 mg CuI and 117 mg L-proline in dimethylsulfoxide (1 mL) was added to reaction mixture. Then 3 mL 2M dimethylamine in tetrahydrofurane was added to reaction mixture. After stirring overnight, the reaction mixture was cooled to room temperature, diluted with water (20 mL) and extracted with ethylacetate (3×20 mL). After separation, organic layer was dried and concentrated to dryness. After high vacuum, 650 mg residue was obtained. 650 mg of (7c) with purity about 46% LCMS were obtained. The product was purified by flash chromatography ($H_2O$ (+0.1% formic acid)/acetonitrile).

Example 11—Synthesis of (8c) from (7c)—Deprotection by Benzylether Cleavage 290 mg (0.743 mmol) of (7c) were dissolved in dry acetonitrile (2.5 mL). 2.5 mL of HBr (48%) was added and the reaction mixture was stirred at 80° C. After 2 h, another 1 mL of HBr (48%) was added to reaction mixture. The mixture was stirred overnight at 80° C. Reaction mixture was cooled to room temperature, then diluted with acetonitrile (10 mL). After filtration, filtrate was concentrated to dryness. 700 mg residue was obtained. Purification has been performed by prep. HPLC (C18, $H_2O$/acetonitrile, 0.1% formic acid). 33 mg pure product were obtained (NMR showed purity over 95%).

Example 12—Synthesis of (7d) from (6)—Amination $K_2CO_3$ was dried under high vacuum. 97 mg (0.5 mmol) CuI, 117 mg (1.02 mmol) L-proline were added to dry dimethylsulfoxide (2 mL) under $N_2$ condition. After this, 0.8 g (1.7 mmol) (6) and 467 mg (3.4 mmol) dry $K_2CO_3$ were added to reaction. 546 mg 2,2-Difluoroethylamine was added to reaction mixture. After addition, reaction was heated to 100° C. After stirring overnight, the reaction mixture was cooled to room temperature. Then it was diluted with $H_2O$ (20 mL) and extracted with ethylacetate (3×30 mL). After separation, organic layer has been dried and concentrated to dryness. 1 g of (7d) was obtained. After 1 h high vacuum, 0.8 g (7d) was obtained. The product was purified by flash chromatography ($H_2O$ (+0.1% formic acid)/acetonitrile).

Example 13—Synthesis of (8d) from (7d)—Deprotection by Benzylether Cleavage

Two reactions were carried out with different fractions (different purity). A) 160 mg (0.375 mmol) of (7d) were dissolved in dry acetonitrile (1.3 mL). 1.3 mL of HBr (48%) was added and the reaction mixture was stirred at 80° C. After 5 h, it was cooled to room temperature. B) 100 mg (0.375 mmol) of (7d) were dissolved in dry acetonitrile (1.3 mL). 1.3 mL of HBr (48%) was added and the reaction mixture was stirred at 80° C. After 5 h, it was cooled to room temperature. Then another 0.4 mL of HBr (48%) for each reaction was added. After another 1.5 h, heating was stopped. After it was cooled to room temperature, the reaction mixture was filtrated. Filtrate was concentrated to dryness. 400 mg residue was obtained. Reaction B was not finished until another 0.6 mL of HBr (48%) was added. 700 mg residue was obtained. The crude product was purified by prep. HPLC ($C_{18}$, $H_2O$/acetonitrile, 0.1% formic acid). After concentration, Reaction A: 20 mg pure product by LCMS (NMR showed purity is about 90%). Reaction B: 20 mg pure product by LCMS, NMR showed purity is about 80%.

Example 14—Insulin Secretion from Pancreatic Islets In Vivo

Insulin secretion was tested after administration of compounds (4), (5), (8a), (8b), (8c) and (8d) in an animal model and compared to dextrorphan (DXO).

Mouse pancreatic islets were treated with a low, non-stimulatory glucose concentration (2 mM) or a high, stimulatory glucose concentration (20 mM) in the absence or presence of 10 µM test compound. Insulin secretion was determined as percent of basal control, and values are expressed as means+/−SD (N=3). The asterisks (*) indicate p values smaller than 0.05 in Student's t-tests. The results are shown in FIGS. 2 to 4.

Figure 2:
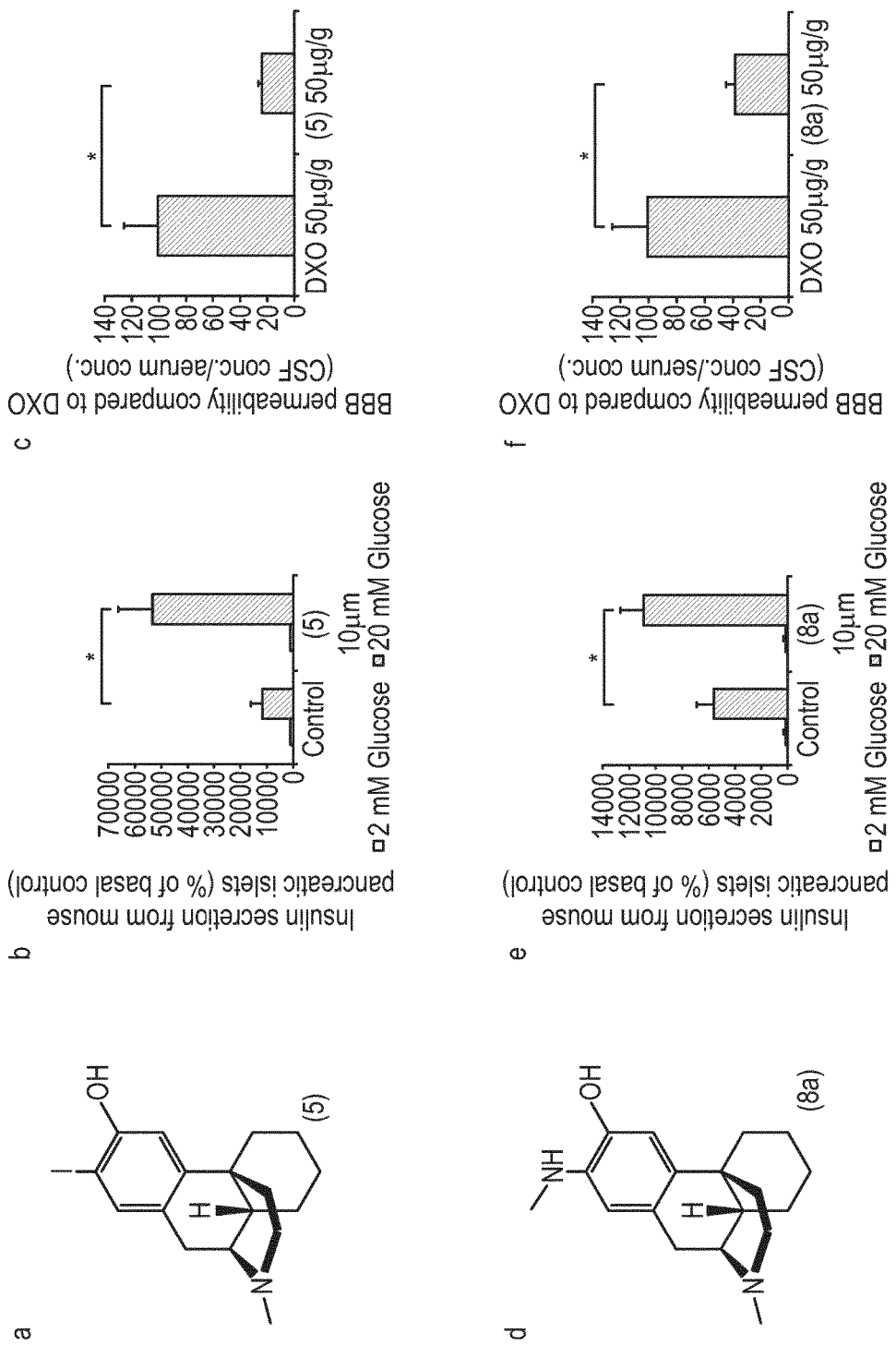
FIG. 2 shows the chemical structures, graphical representations of insulin secretion from mouse pancreatic islets and BBB (blood brain barrier) permeability compared to DXO for exemplary compounds (5) and (8a).

FIG. 2: (FIG. 2 a,d) Chemical structure of compound (5) (FIG. 2 a) and compound (8a) (FIG. 2 d). (FIG. 2 b,e) Insulin secretion from mouse pancreatic islets without (control) and with 10 µM compound (5) (FIG. 2 b) and compound (8a) (FIG. 2 e) at 2 mM glucose (white columns) and 20 mM glucose (black columns); n=3-4 islet batches each. (FIG. 2 c,f) Blood brain barrier (BBB) permeability of dextrorphan (DXO) compared to BBB permeability of compound (5) (FIG. 2 c) and compound (8a) (FIG. 2 f) determined in C57BL/6 mice approximately 30 min after intraperitoneal (i.p.) injection of glucose (1.5 mg $g^{-1}$ body weight) together with either 50 µg $g^{-1}$ body weight of DXO or 50 µg $g^{-1}$ body weight of one of the compounds; n=19 mice for DXO and n=3-5 mice for the compounds. Significance determined by Student's t-test. *P<0.05. All values are mean±SD.

Figure 3:
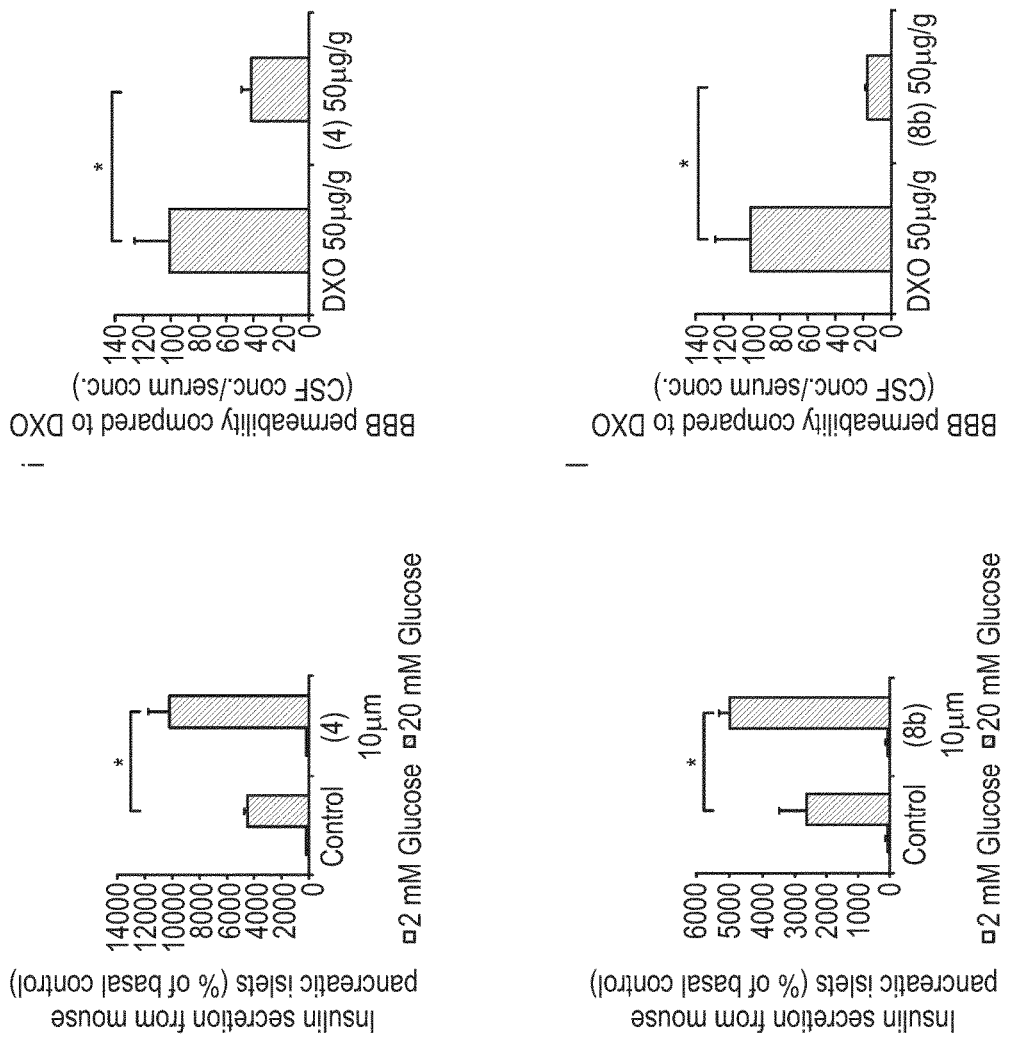
FIG. 3 shows the chemical structures, graphical representations of insulin secretion from mouse pancreatic islets and BBB (blood brain barrier) permeability compared to DXO for exemplary compounds (4) and (8b).

FIG. 3: (FIG. 3 g,j) Chemical structure of compound (4) (FIG. 3 g) and compound (8b) (FIG. 3 j). (FIG. 3 h,k) Insulin secretion from mouse pancreatic islets without (control) and with compound (4) (FIG. 3 h) and compound (8b) (FIG. 3 k) at 2 mM glucose (white columns) and 20 mM glucose (black columns); n=3-4 islet batches each. (FIG. 3 i,l) Blood brain barrier (BBB) permeability of dextrorphan (DXO) compared to BBB permeability of compound (4) (FIG. 3 i) and compound (8b) (FIG. 3 l) determined in C57BL/6 mice approximately 30 min after intraperitoneal (i.p.) injection of glucose (1.5 mg $g^{-1}$ body weight) together with either 50 µg $g^{-1}$ body weight of DXO or 50 µg $g^{-1}$ body weight of one of the compounds; n=19 mice for DXO and n=3-5 mice for the compounds. Significance determined by Student's t-test. *P<0.05. All values are mean±SD.

Figure 4:
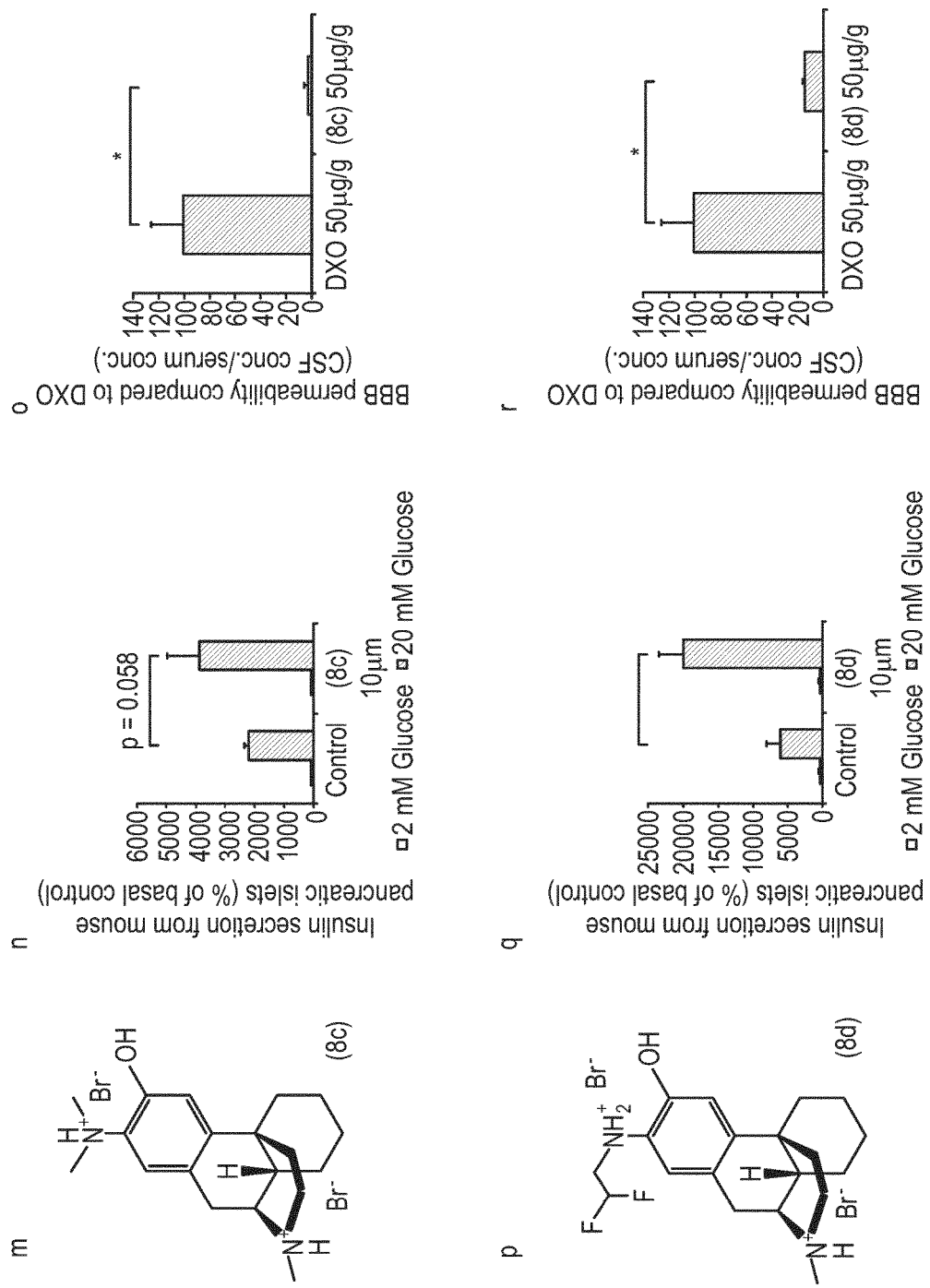
FIG. 4 shows the chemical structures, graphical representations of insulin secretion from mouse pancreatic islets and BBB (blood brain barrier) permeability compared to DXO for exemplary compounds (8c) and (8d).

FIG. 4: (FIG. 4 m,p) Chemical structure of the compound (8c) (FIG. 4 m) and compound (8d) (FIG. 4 p). (FIG. 4 n,q) Insulin secretion from mouse pancreatic islets without (control) and with compound (8c) (FIG. 4 n) and compound (8d) (FIG. 4 q) at 2 mM glucose (white columns) and 20 mM glucose (black columns); n=3-4 islet batches each. (FIG. 4 o,r) Blood brain barrier (BBB) permeability of dextrorphan (DXO) compared to BBB permeability of compound (8c) (FIG. 4 o) and compound (8d) (FIG. 4 r) determined in C57BL/6 mice approximately 30 min after intraperitoneal (i.p.) injection of glucose (1.5 mg $g^{-1}$ body weight) together with either 50 µg $g^{-1}$ body weight of DXO or 50 µg $g^{-1}$ body weight of one of the compounds; n=19 mice for DXO and n=3-5 mice for the compounds. Significance determined by Student's t-test. *P<0.05. All values are mean±SD.

Example 15—Blood Glucose Concentrations In Vivo

Blood glucose concentrations were measured after administration of compound (4) in an animal model and compared to dextrorphan (DXO).

Fasted 8 week-old male C57BL/6 mice received an i.p. injection of glucose (1.5 mg per g (body weight)) at the point of time 0' minutes (control) or glucose together with compound (4) (100 µg per g (body weight)) and DXO (50 µg per g (body weight)) at the point of time 0 minutes. Blood glucose levels were determined at the indicated times in FIG. 5. Values are expressed as means+SD (n=6 mean values per group). P values with Student's t-test.

Figure 5:
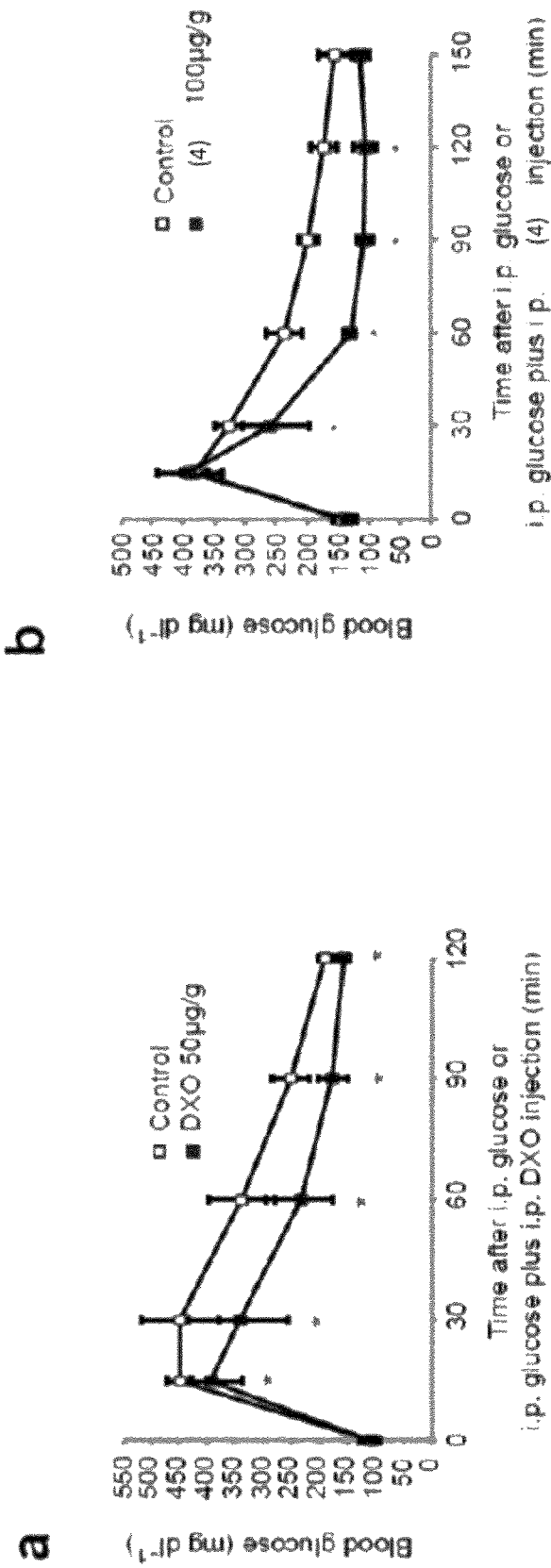
FIG. 5 is a graphical representation of blood glucose concentrations in mice with or without i.p injection of 50 μg $g^{-1}$ bodyweight DXO, or 100 μg $g^{-1}$ bodyweight exemplary compound (4).

FIG. 5: (FIG. 5 a,b) Blood glucose concentrations of control mice during an i.p. glucose (1.5 mg $g^{-1}$ body weight) tolerance test with or without i.p. injection of 50 µg $g^{-1}$ body weight DXO (FIG. 5 a) or 100 µg $g^{-1}$ body weight compound (4) (FIG. 5 b); n=7-8 male mice each. *P<0.05.

Figure 6:
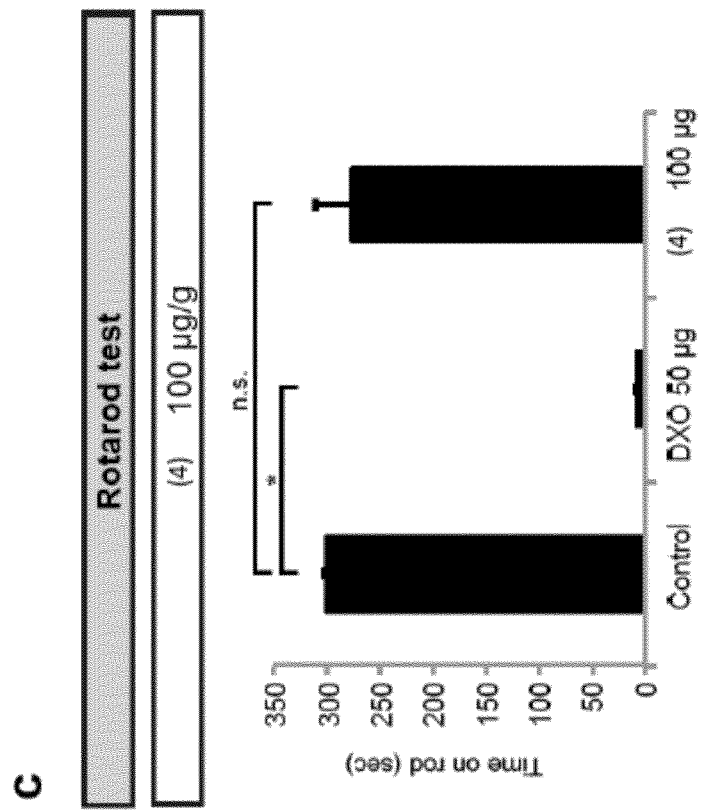
FIG. 6 is a graphical representation of a rotarod test measuring time on rod after i.p. injections of PBS without (control), or with 50 μg $g^{-1}$ bodyweight DXO, or with 100 μg $g^{-1}$ bodyweight exemplary compound (4).

FIG. 6: Time that C57BL/6 mice stayed on rod 30 minutes after i.p. injection of PBS without (control) or with either 50 µg $g^{-1}$ body weight DXO or 100 µg $g^{-1}$ body weight compound (4); n=5 male mice each. Significance determined by Student's t-test. *P<0.05. All values are mean±SD.

Figure 7:
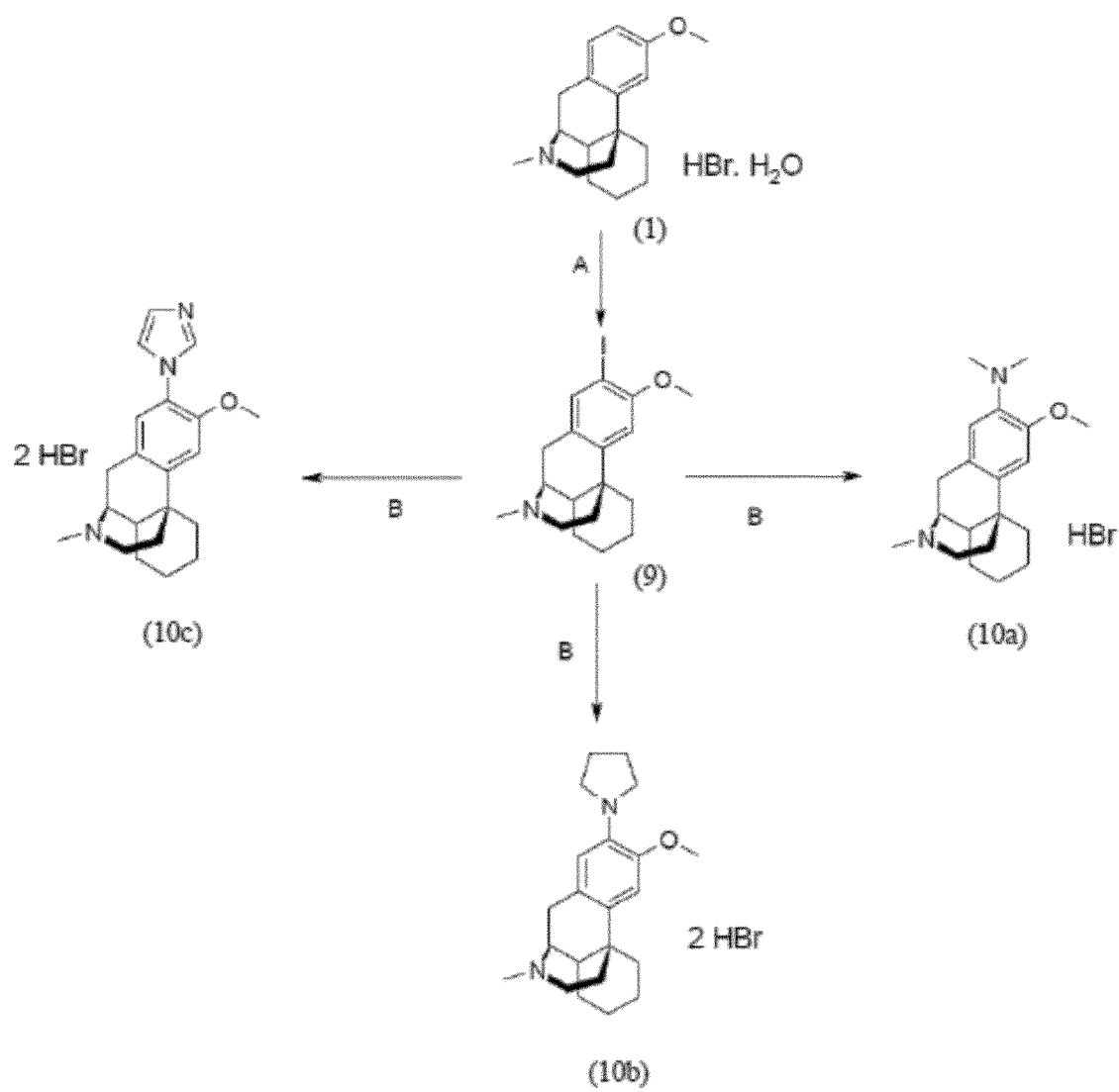
FIG. 7 is a general overview of the route for synthesizing further exemplified dextrorphan-derivatives of the present invention.

FIG. 7: General overview over the route for synthesizing further exemplified dextrorphan-derivatives of the invention:

Example 16—Synthesis of (9) from (1)—Iodation

Alternative a) 3 g of Dextromethorphan hydrobromide monohydrate were dissolved in 50 mL $CHCl_3$. It was washed 2 times with 35 mL IN NaOH-solution. The organic phase was dried over MgSO₄, filtered off and the solvent was removed under reduced pressure. Yield=2.15 g (purity 99%).

Alternative b) 2 g (7.37 mmol) Dextromethorphan were dissolved in 55 mL ethanol. It was added 4.6 g (14.74 mmol) silver sulfate and 3.74 g (14.74 mmol) iodine. The mixture was stirred at RT overnight. Reaction was stopped and filtrated. Filtrate Cake was washed with ethanol. After concentration, 38 g oil was obtained (NMR showed purity of about 40%). 4.3 g (9) were dissolved in DCM, evaporated on 5 g ISOLUTE® HM-N (diatomaceous earth) and purified With Grace Reveleris. Column: CHROMABOND Flash with 80 g MN RP 18. Mobile phase H₂O (+0.1 HCOOH)/acetonitrile (product purity about 95% by NMR and LCMS).

Example 17—Synthesis of (10a) from (9)—Amination 10.0 g (0.02517 mol) of (9), 6.96 g (00050340 mmol) K₂CO₃ (dried in high vacuo), 1.45 g CuI (0.007598 mol) and 17.5 g (0.01497 mol) L-proline were placed in a 250 mL Parr-reactor. 95 mL DMSO dry were added under N₂ and 3×10 bar N₂ were pressed to the reactor. 50.3 mL dimethylamine 2M in THF were added under N₂ conditions, the reactor was closed and heated to 90° C. Work-up: The reaction mixture was cooled to room temperature, diluted with H₂O (700 mL) and extracted three times with EtOAc (300 mL). The organic phase was washed with two times diluted aqueous ammonia (250 mL), dried with MgSO₄, filtered and evaporated to dryness. Compound (10a) was further purified by chromatography.

Example 18—Synthesis of (10b) from (9)—Pyrrolidination

Apparatus: Microwave Vial (20 mL), magnetic stirrer, reaction dry and under nitrogen. Procedure: Compound (9) (500 mg; 1.258 mmol), K₂CO₃ (349 mg; 2.523 mmol), CuI (73 mg; 0,382 mmol), L -Proline (88 mg; 0764 mmol) were suspended in DMSO (1 7 mL) and treated with pyrrolidine (407.98 mg). The resulting mixture was stirred at 100° C. The reaction mixture was treated with H₂O (60 ml), a solid felt out and this was filtered, washed with H₂O (20 mL) and dried under high vacuum. Compound (10b) was further purified by chromatography.

Example 19—Synthesis of (10c) from (9)—Imidazolination

Apparatus: Microwave Vial (20 mL), magnetic stirrer, reaction dry and under nitrogen. Procedure: Compound (9) (500 mg; 1.258 mmol), K₂CO₃ (349 mg; 2.523 mmol), CuI (73 mg; 0,382 mmol), L -Proline (88 mg; 0764 mmol) were suspended in DMSO (1.7 mL) and treated with imidazole (407.88 mg). The resulting mixture was stirred 36 hours at 100° C. 1 eq imidazole (407 mg) and 1 eq CuI (73 mg) were added at room temperature and the reaction mixture was stirred at 100° C. overnight. Imidazole (50 mg) and CuI (14 mg) were added at room temperature and the reaction mixture was stirred at 100° C. The reaction was stopped and worked up. The reaction mixture was treated with H₂O (60 mL), a solid felt out and this was filtered, washed with H₂O (20 ml) and dried under high vacuo. The filtrate was extracted With EtOAc (3×50 ml). The organic phase was dried over MgSO₄ and the solvent was removed in vacuo. Compound (10c) (769 mg) was obtained as yellow oil. Compound (10c) was further purified by chromatography.

Example 20—Blood Glucose Concentrations In Vivo

In accordance with Example 15, blood glucose concentrations were measured after administration of compounds (10a), (10b) and (10c) in an animal model and compared to dextromethorphan (DXM).

FIG. 8: Chemical structure of compound (10a) (FIG. 8*a*), compound (10b) (FIG. 8*d*) and compound (10c) (FIG. 8*g*). (FIG. 8*b,e,h*) Insulin secretion from mouse pancreatic islets without (control) and with 10 μM compound (10a) (FIG. 8*b*), compound (10b) (FIG. 8*e*) and compound (10c) (FIG. 8*h*) at 2 mM glucose (white columns) and 20 mM glucose (black columns); n=4-6 islet batches each. (FIG. 8*c,f,i*) Blood brain barrier (BBB) permeability of dextromethorphan (DXM) compared to BBB permeability of compound (10a) (FIG. 8*c*), compound (10b) (FIG. 8*f*) and compound (10c) (FIG. 8*i*) determined in C57BL/6 mice approximately 30 min after oral application of glucose (1.5 mg/g body weight) together with either DXM or of one of the compounds; concentrations as indicated in the figure; n=4-8 mice for DXM and n=4-5 mice for the compounds. Significance determined by Student's t-test. * P<0.05. All values are ±SD.

Figure 9A:
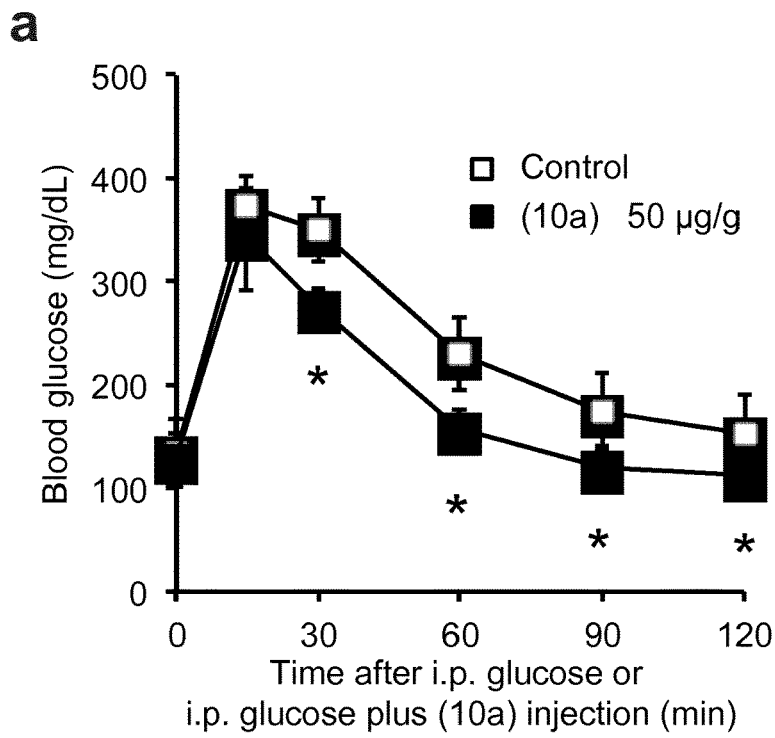
FIG. 9a-c are graphical representations of blood glucose concentrations in mice with or without i.p injection of 50 μg $g^{-1}$ bodyweight exemplary compounds (10a), (10b), or (10c).
Figure 9B:
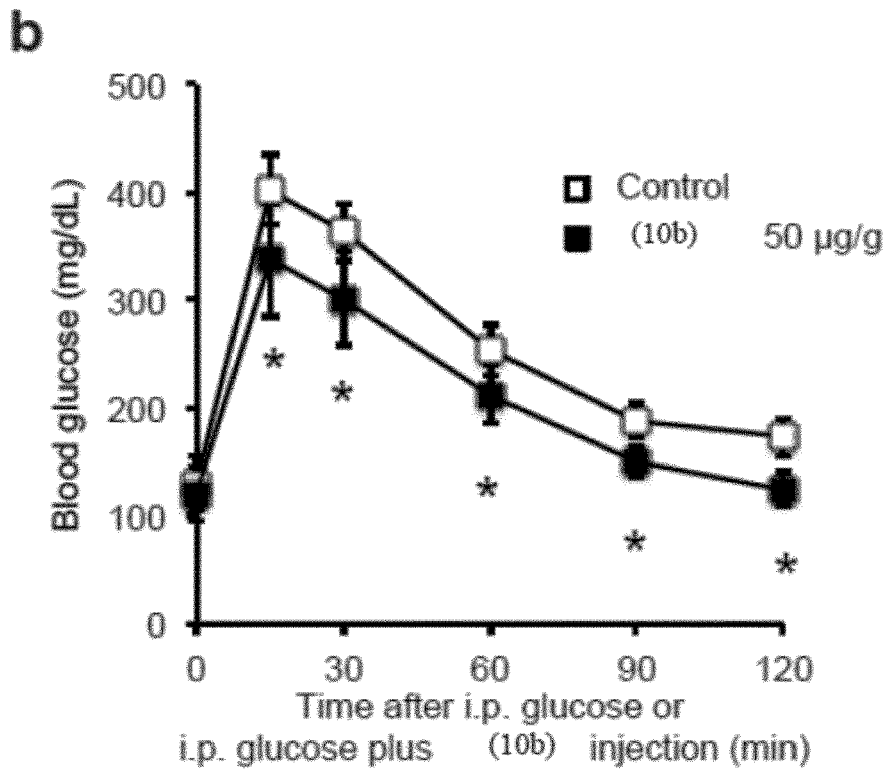
Figure 9C:
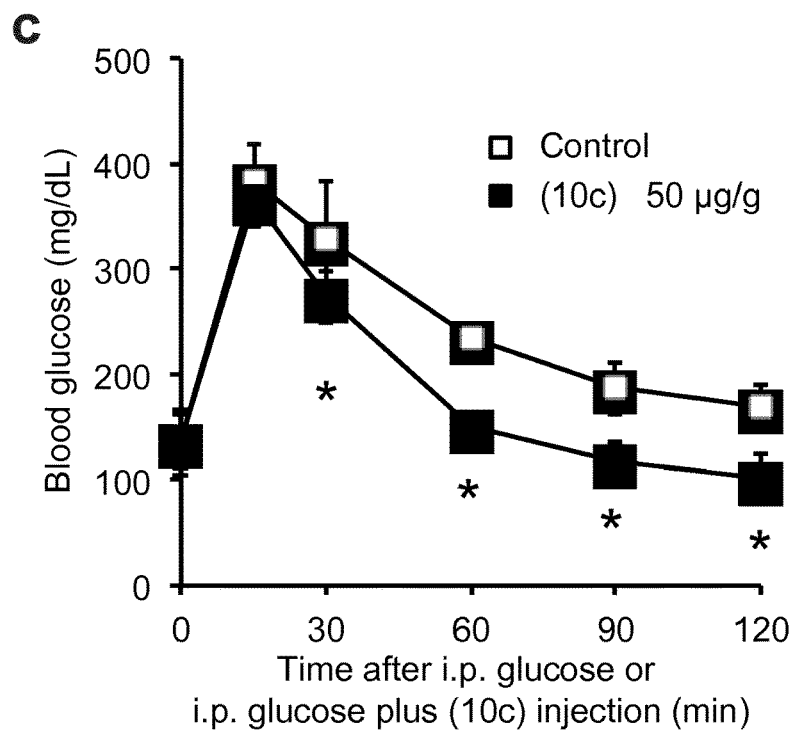

FIG. 9: Blood glucose concentrations of control mice during an i.p. glucose (1.5 mg/g body weight) tolerance test with or without i.p. injection of 50 μg/g bodyweight compound (10a) (FIG. 9*a*), compound (10b) (FIG. 9*b*) or compound (10c) (FIG. 9*c*); n=7-8 male mice each. Significance determined by Student's t-test. * P<0.05. All values are ±SD.

Figure 10:
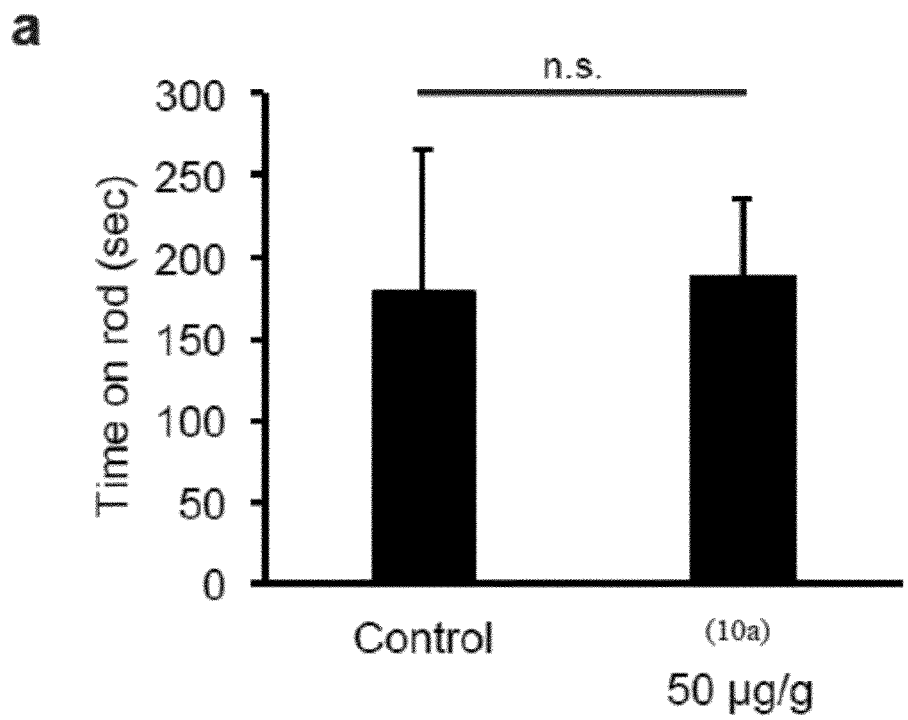
FIG. 10 is a graphical representation of a rotarod test measuring time on rod after i.p. injections of PBS without (control) or with 50 μg $g^{-1}$ bodyweight exemplary compound (10a).

FIG. 10: Time that C57BL/6 mice stayed on rod 30 minutes after i.p. injection of PBS without (control) or with 50 μg/g bodyweight compound (10a); n=6 male mice each. Significance determined by Student's t-test. * P<0.05. All values are ±SD.

What is claimed is:
1. A method for the treatment of insulin-dependent diabetes mellitus or non-insulin-dependent diabetes mellitus which comprises the administration to a subject in need thereof of an effective amount of one or more compounds according to general formula (I)

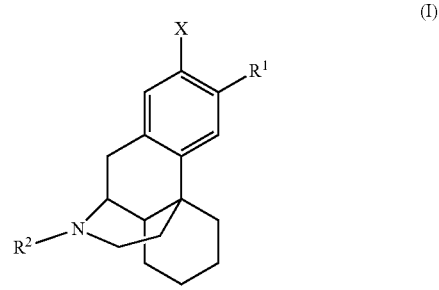

wherein
R¹ is selected from —OH, —CO₂H, —R⁰, —OR⁰, —OC(=O)R⁰, —OC(=O)OR⁰ or —OC(=O)NHR⁰;
R² is selected from —H, —R⁰, —C(=O)R⁰, —C(=O)OR⁰, —C(=O)NHR⁰, or —C(=NH)—NH—C(=NH)—NH₂;

X is selected from —F, —Cl, —Br, —I, or —NR$^3$R$^4$, wherein R$^3$ and R$^4$ are independently of one another selected from —H or —R$^0$; or wherein R$^3$ and R$^4$ together with the nitrogen atom to which they are attached form a three, four, five, six, or seven membered heterocycloalkyl- or heteroaryl-ring, in each case independently unsubstituted or substituted;

wherein R$^0$ is in each case independently selected from —C$_1$-C$_6$-alkyl, -aryl, -heteroaryl, —C$_1$-C$_6$-alkyl-aryl or —C$_1$-C$_6$-alkyl-heteroaryl, in each case independently unsubstituted or substituted;

or its physiologically acceptable salt and/or stereoisomer, including mixtures thereof in all ratios.

2. The method according to claim 1, wherein X is —NR$^3$R$^4$, wherein R$^3$ and R$^4$ are independently of one another selected from —H or —C$_1$-C$_6$-alkyl or —C$_1$-C$_6$-fluoroalkyl.

3. The method according to claim 2, wherein X is —NH$_2$, —NHCH$_3$, —NHCH$_2$CH$_2$F, —NHCH$_2$CHF$_2$, —N(CH$_3$)$_2$, or —NHCH$_2$CH$_3$.

4. The method according to claim 1, wherein X is —NR$^3$R$^4$, wherein R$^3$ and R$^4$ together with the nitrogen atom to which they are attached form a four membered, five membered, six membered or seven membered heterocycloalkyl- or heteroaryl-ring, in each case independently unsubstituted or substituted.

5. The method according to claim 4, wherein X is —NR$^3$R$^4$, wherein R$^3$ and R$^4$ together with the nitrogen atom to which they are attached form a pyrrolidine ring or imidazole ring, in each case independently unsubstituted or substituted.

6. The method according to claim 1, wherein X is —I.

7. The method according to claim 1, wherein R$^1$ is —OH, —OC$_1$-C$_6$-alkyl, unsubstituted or substituted, or —C$_1$-C$_6$-alkyl, unsubstituted or substituted.

8. The method according to claim 7, wherein R$^1$ is —OH, —OCH$_3$, or —CH$_3$.

9. The method according to claim 8, wherein R$^1$ is —OCH$_3$.

10. The method according to claim 1, wherein R$^2$ is —H or —C$_1$-C$_6$-alkyl.

11. The method according to claim 10, wherein R$^2$ is —CH$_3$.

12. The method according to claim 1, which has a stereochemistry according to general formula (II)

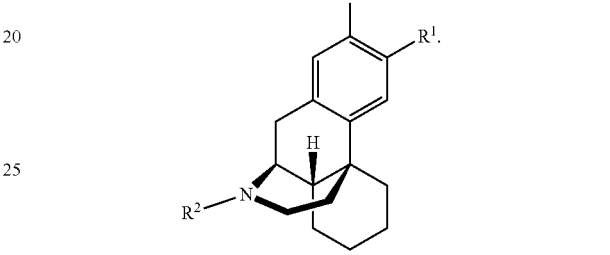

(II)

* * * * *